United States Patent
Zhang et al.

(10) Patent No.: US 9,286,061 B2
(45) Date of Patent: Mar. 15, 2016

(54) GENERATING AND MANAGING ELECTRONIC DOCUMENTATION

(75) Inventors: Kuo Zhang, Beijing (CN); Yushun Wang, Beijing (CN); Michael T Gillam, Washington, DC (US); Xiaopei Zhang, Beijing (CN); Yan Yu, Beijing (CN)

(73) Assignee: Microsoft Technology Licensing, LLC, Redmond, WA (US)

( * ) Notice: Subject to any disclaimer, the term of this patent is extended or adjusted under 35 U.S.C. 154(b) by 987 days.

(21) Appl. No.: 12/967,820

(22) Filed: Dec. 14, 2010

(65) Prior Publication Data

US 2012/0151382 A1  Jun. 14, 2012

(51) Int. Cl.
*G06F 9/44* (2006.01)
*G06F 19/00* (2011.01)
*G06F 17/30* (2006.01)

(52) U.S. Cl.
CPC ............ *G06F 8/73* (2013.01); *G06F 17/30011* (2013.01); *G06F 19/322* (2013.01)

(58) Field of Classification Search
CPC ....... G06Q 50/22; G06Q 10/10; G06F 19/322; G06F 19/321; G06F 19/3412; G06F 19/3431; G06F 19/3443; G06F 19/345; G06F 19/3462; G06F 19/363; G06F 3/0487; G06F 3/1423
USPC .......................................................... 715/752
See application file for complete search history.

(56) References Cited

U.S. PATENT DOCUMENTS

| | | | |
|---|---|---|---|
| 6,684,188 B1 | 1/2004 | Mitchell et al. | |
| 8,103,952 B2* | 1/2012 | Hopp .................. | G06F 17/2247 715/234 |
| 8,533,604 B1* | 9/2013 | Parenti .................. | G06F 9/4443 715/707 |
| 2003/0103071 A1 | 6/2003 | Lusen et al. | |
| 2005/0022111 A1* | 1/2005 | Collet .................. | G06F 17/246 715/205 |
| 2007/0033535 A1* | 2/2007 | Cornacchia, III ..... | G06F 19/322 715/762 |
| 2007/0245308 A1* | 10/2007 | Hill ..................... | G06F 17/2247 717/114 |
| 2008/0208631 A1 | 8/2008 | Morita et al. | |
| 2008/0288259 A1* | 11/2008 | Chambers .............. | G10L 15/22 704/275 |
| 2009/0024411 A1 | 1/2009 | Albro et al. | |
| 2009/0031230 A1* | 1/2009 | Kesler .................. | 715/764 |
| 2009/0164474 A1* | 6/2009 | Noumeir ............... | G06F 19/321 |
| 2009/0265187 A1 | 10/2009 | Boone et al. | |
| 2010/0082372 A1 | 4/2010 | Wen et al. | |
| 2010/0138231 A1* | 6/2010 | Linthicum et al. ................ | 705/2 |
| 2011/0041140 A1* | 2/2011 | Harm ................... | G06F 9/4843 719/318 |

OTHER PUBLICATIONS

Brelstaff, et al., "Internet Patient Records: new techniques", retrieved on Aug. 25, 2010 at <<http://www.jmir.org/2001/1/e8/>>, Journal of Medical Internet Research, vol. 3, No. 1, 2001, pp. 1-8.

Kuhn, et al., "Structured Data Collection and Knowledge-Based User Guidance for Abdominal Ultrasound Reporting", retrieved on Aug. 23, 2010 at http://www.ncbi.nlm.nih.gov/pmc/articles/PMC2248524/pdf/procascamc00002-0331.pdf>>, McGraw-Hill, Inc., AMIA Symposium on Computer Applications in Medical Care, Washington, D.C., 1994, pp. 311-315.

Watzlaf, et al., "Testimony of the American Health Information Management Association to the Standards and Security Subcommittee of the National Committee on Vital and Health Statistics", retrieved on Aug. 25, 2010 at http://library.ahima.org/xpedio/groups/public/documents/ahima/bok1_018867.hcsp?dDocName=bok1_018867>>, American Health Information Management Association, Jul. 26, 2005, pp. 1-12.

\* cited by examiner

*Primary Examiner* — Sherrod Keaton
(74) *Attorney, Agent, or Firm* — Steve Wight; Sandy Swain; Micky Minhas

(57) ABSTRACT

Some implementations provide a user interface for generating an electronic document. An external component may be launched within the user interface for accessing external data, and context data of the current document may be provided to the external component. The external data that corresponds to the context data for the document may be displayed within the user interface, such as for enabling a user to interact with the data and/or include a portion of the data in the document.

20 Claims, 20 Drawing Sheets

Title 518

File | Home 506

Cut / Copy / Paste — CLIPBOARD 508 | B I U / A A — FONT 510 | ≡ ≡ ≡ / ≡ ≡ ≡ — PARAGRAPH 512 | Add / Anchor 514 — Previous / Next | Undo / Redo — UNDO 516

Macro 520 — NEW 522 | EDIT 524 | CLONE 526 | DELETE 528 — 530 / 532

Search — ALL ▽ | ASCENDING

- RADIOLOGY 534
- ACCOUNT 536
- DATE 538
- DIAGNOSIS 540
- DATE OF BIRTH 542
- PATHOLOGY 544
- ALLERGIES 546
- LABS 548

SOAP Note

Chief Complaint
chest pain is moderately severe, constant, lasts 5-10 minutes, dull and aching in quality, radiates to the left shoulder, is associated with shortness of breath, nausea, and diaphoresis

Lab Results

Radiology
Radiology Readings

| 1 | EXAMPLE HOSPITAL ACCOUNT: 41070022 | 10/9/2009 | OBSV: OCT 9 2009 | BY: RADPRVT ORDERING, FINAL |
| | EXAMPLE RADIOLOGY TEST RESULT | | | |

1702 TERMINOLOGY STORAGE AND EXCHANGE: DIAGNOSIS==MYOCARDIAL INFARCTION

Differential Diagnosis
MYOCARDIAL INFARCTION

Plan
Continue close observation

GENERATING AND MANAGING ELECTRONIC DOCUMENTATION

BACKGROUND

In recent years, the health care community has made an effort to adopt electronic documentation of medical records. Electronic clinical documentation can provide direct benefits in efficiency and accuracy of patient treatment, can reduce costs associated with coding and billing, and can improve management and administration of medical resources and personnel. Thus, use of electronic documentation can improve the effectiveness of many aspects of the healthcare system. However, conventional electronic clinical documentation solutions have a poor track record of actually being used by health care providers. For example, some research shows that electronic formats account for only a small percentage of all clinical documentation. One reason for this low level of use is that doctors report as much as a 50% increase in time spent preparing documentation following the adoption of electronic documentation systems.

Traditional clinical documentation is typically a "linear input" user experience in which a health care provider starts to write a document, and when he or she wants to reference an external data source, such as a lab report, the health care provider saves a draft of the document, jumps to a lab module, remembers or copies particular data from the lab report, goes back to the document, and enters or pastes the lab data into the document. This process may be repeated a number of times during preparation of a document, can be very time consuming, and may introduce errors caused by human mistake. Thus, conventional systems may allow a user to copy and paste data into documentation, but the user may have to jump back and forth through different modules, which risks losing the context of the current input. Further, some conventional electronic documentation systems use macros to retrieve data from other systems for inputting the data into clinical documentation, but users can have difficulties remembering all of the macros and/or harmonizing new data into a current document.

Another challenge in electronic clinical documentation is providing a hybrid data entry mode for enabling input of both structured data and unstructured data into a document. For example, a diagnosis may contain a large number of medical terms, and typically each of these terms may be defined in SNOMED CT® (Systematized Nomenclature of Medicine—Clinical Terms). In conventional electronic documentation solutions, a care provider may have a difficult time identifying each SNOMED-defined term and inputting the term into the electronic documentation system, and thus, might leave some terms out. However, providing a complete and accurate record may be important for correct diagnosis, treatment and the like. Further, while there has been a large amount of research related to the use of natural language processing (NLP) in electronic document creation, NLP is typically not widely used in a clinical environment because even a small error rate in word recognition may cause a serious patient safety issue and/or may contribute to lowered efficiency because the health care provider may have to carefully proofread each entry to protect against errors.

SUMMARY

This Summary is provided to introduce a selection of concepts in a simplified form that are further described below in the Detailed Description. This Summary is not intended to identify key or essential features of the claimed subject matter; nor is it to be used for determining or limiting the scope of the claimed subject matter.

Some implementations disclosed herein provide for electronic documentation generation and management by providing a user interface for generating documentation that incorporates external data from one or more external sources. In some implementations, the user interface is able to launch external components to provide access to the external data within the user interface. Further, in some implementations, context data may be provided to a launched component to ensure that the launched component provides data relevant to a current document.

BRIEF DESCRIPTION OF THE DRAWINGS

The detailed description is set forth with reference to the accompanying drawing figures. In the figures, the left-most digit(s) of a reference number identifies the figure in which the reference number first appears. The use of the same reference numbers in different figures indicates similar or identical items or features.

FIG. 15 is an example user interface illustrating triggering structured data input.

FIG. 17 is an example user interface illustrating terminology storage and exchange.

FIG. 20 is an example user interface illustrating formatted input based on outbound data.

DETAILED DESCRIPTION

Electronic Documentation

Figure 1:
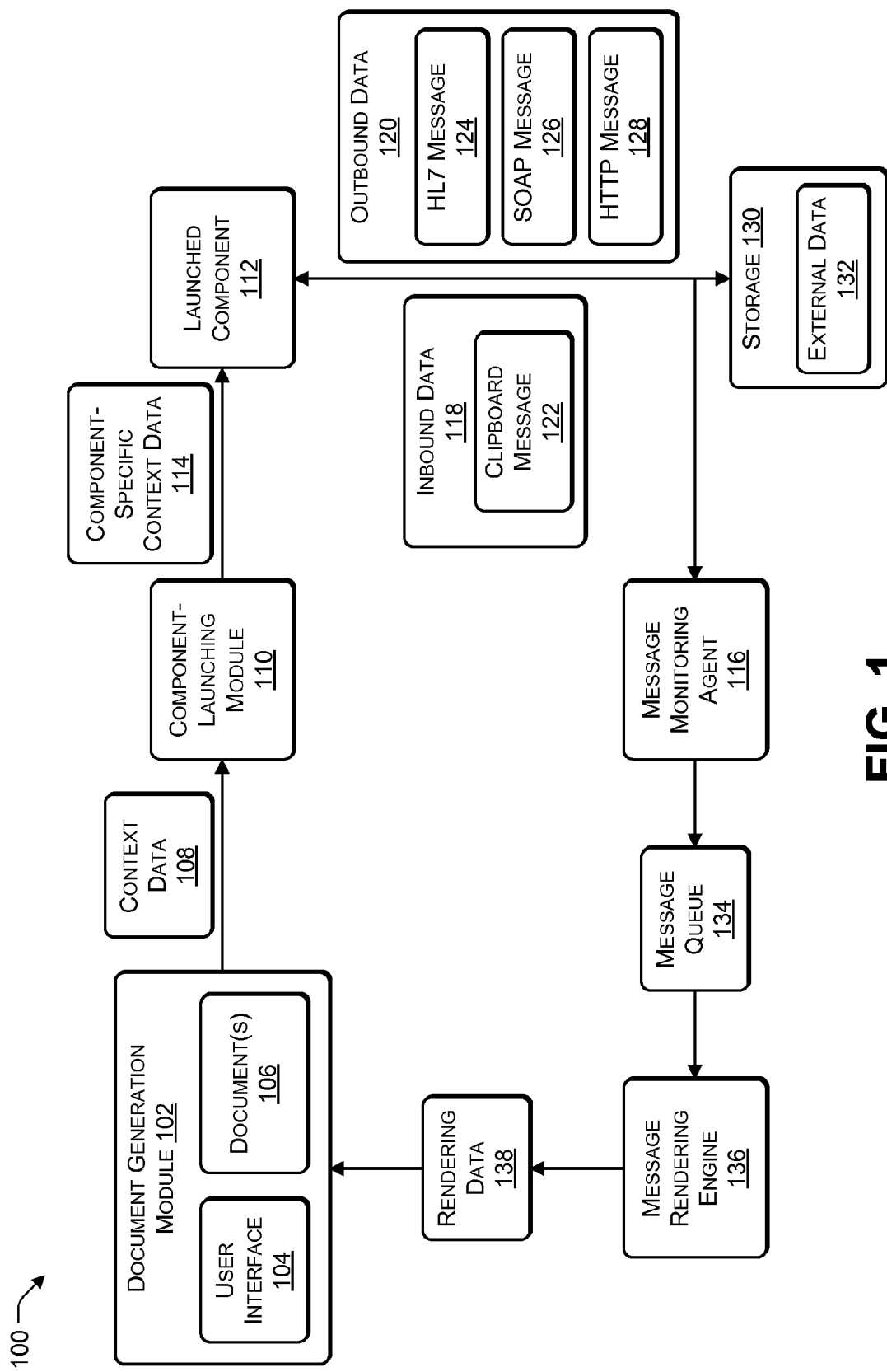
FIG. 1 is a block diagram of an example framework for electronic documentation generation and management according to some implementations.

The technologies herein may be applied to generation and management of electronic documentation, such electronic medical records, legal documents, financial documents, and other documents that incorporate data from a variety of external or third-party applications or other external data sources. Some implementations herein provide a non-linear technique for generating electronic documentation through launching of external components within the context of current documentation. For example, a context of a document may be automatically ascertained and maintained based on a current subject of the document, a current author of the document, and/or other context information that may be determined for the document. Thus, when a component or application for obtaining data from an external data source is launched or initialized, the context data for the current document may be provided to the component in a compatible format or protocol. Providing the context data directly to the component can ensure that the component accesses and returns correct information appropriate for the context of the document that is currently being generated.

As an example, in a typical health care environment, a patient's data may be spread throughout a number of different departments and databases within a health care institution. For instance, radiology, pathology, labs, pharmacy, billing, various departments and specialties, etc., may each have their own separate databases. Further, each separate database may contain different types of data and may utilize different third-party modules, applications or components (hereafter "components") for accessing the particular different types of data. Accordingly, some implementations herein enable launching external or third-party components from within a current document for retrieving data content from various remotely located external data sources for entry into the current document. For example, the data content of the various different types may be obtained dynamically from the launched components through a single uniform document generation user interface. Further, the user creating the document may launch a component at any time during document creation of a document, as desired, without having to follow a predetermined format or pattern for data entry. Thus, implementations herein provide for smooth user interaction with external data sources available through launched components for entry of external data into a current document. Additionally, some implementations provide for dynamically rendering a layout to fit retrieved external data content into current documentation. For example, implementations may enable a hybrid framework for inputting both structured and unstructured data into a current document.

According to one possible example, when a doctor or other health care provider generates an electronic clinical document, the context of this documentation may be automatically determined and recorded as context data. Examples of such context data may include: patient name or identification; a condition, symptoms, or a diagnosis of the patient; a health care provider institution and/or department; a current date or time; a current location of the patient; a doctor name or other health care provider identification; access privileges of the person preparing the document, and the like. This context information may be used by a component launcher to launch other components from within a user interface being used to prepare the document. For example, external components, such as third-party-vendor components, applications, modules, or plug-ins may be launched through appropriate protocols and commands. Thus, the launching mechanism can be varied according to particular system implementations, such as Object Linking and Embedding (OLE)/Distributed Component Object Model (DCOM)/.Net Framework or other plug-in framework. A component being initialized from within the user interface may receive relevant context data passed from the component launching module in a format or protocol that the component can recognize. The component can then use this context data to open the relevant data with appropriate settings and/or desired information. For example, a launched component might open a spreadsheet for a current patient with the latest available data relevant to the condition or subject of the document that is being prepared.

Additionally, according to some implementations, when a component is launched, a message monitoring agent may be initialized to monitor the content flow of the launched component. For example, inbound content may be obtained directly from a component through actions by the user such as a "copy to clipboard" action. Outbound content may also be obtained from a component through messages written by the component back to storage, such as to a server or other external computing device that stores data for the launched component, or other location where the relevant data is stored. For example, as a user interacts with a component and the information available through the component, the component may write messages back to a server with which the component communicates. Consequently, a user may cause an open component to trigger out various messages, such as a computerized physician order entry (CPOE) dialogue to update medication or dosages, call out a lab viewer to review a patient's complete blood count (CBC) data, launch a pathology report to read the latest pathology results, etc. The monitoring agent in the documentation framework may intercept any inbound or outbound data for placement into a message queue.

If the user causes the component to send outbound messages during use of the component, the messages containing outbound data, such as modified or updated data, can be automatically placed in the message queue and provided to a rendering engine for possible inclusion in the current document. For example, when the user has finished the review or update of information in a launched component, submitted changes, etc., the documentation framework herein may update the message queue with latest change or information. Further, the documentation framework may render the resulting data and place the result into the current documentation at an appropriate location. Thus, the latest information or any recently updated information may be included in the current document. Implementations herein may also leverage Extensible Stylesheet Language Transformations (XSLT)/parsing language for dynamically rendering a current document that a user is composing.

The techniques, processes and systems for electronic documentation described herein may be implemented in a number of different environments, applications and situations. Consequently, while several examples are described for explanation purposes in the context of electronic documentation of medical records, the disclosure is not limited to the specific examples, and can be extended to additional environments, applications and settings not limited to medical documentation, such as producing legal documents, financial documents, and so forth.

Electronic Documentation Framework

FIG. 1 is a block diagram of an example framework 100 for generating and managing electronic documentation according to some implementations. Framework 100 includes a document generation module 102 that provides a user interface 104 that may be used to generate (i.e., compose) one or more electronic documents 106. For example, a user, such as a doctor or other health care provider may initialize the document generation module 102 and may interact with the user interface 104 to generate the electronic document 106 for carrying out clinical documentation, or the like. During the authoring or generating of the document 106, the document generation module 102 determines and records context data 108 relevant to the document 106 that the user is currently preparing. For example, as mentioned above, context data 108 may include a patient name or other patient identifier, such as a patient ID number; an illness, condition, symptoms, or diagnosis of the patient; a health care institution identification, such as a hospital, clinic and/or department treating the patient; a current date and time; a current location of the patient; a doctor's name or other identifier of a health care provider preparing the document and/or treating the patient; access privileges and/or authorization information of the person preparing the document; and so forth.

As a user prepares the document, the user may refer to one or more external sources of information, such as may be relevant to the patient's diagnosis, treatment, prognosis, etc. For example, the user may wish to enter information regarding the patient's blood work, radiology results, pathology reports, lab results, and the like, into the document 106. Accordingly, the framework 100 enables the user to launch one or more external components from within the user interface 104 and current document 106 to access the relevant information, rather than having to separately access the various external data sources. For example, the user interface 104 may include one or more macros or other command functions that provide instructions to a component-launching module 110 that the user is able to activate for launching a desired launched component 112 to obtain the desired externally-stored information. Furthermore, the component-launching module 110 is able to utilize the context data 108 for the current document 106 when launching a particular component 112 to ensure that the component 112 accesses the correct data relevant to the current document 106. In some implementations, the component launching module 110 includes commands and protocols specific to each available component 112 that can be launched in the user interface 104. Thus, the component launching module 110 is able to provide component-specific context data 114 that ensures that the particular launched component 112 automatically gathers and provides the appropriate information desired by the user generating the document 106.

As discussed above, a component 112 may be an application, plug-in, or the like that is typically provided by a third-party vendor and used for accessing specific types of data on a particular database containing information to be used during generation of the document 106. Thus, the component is an external component because it is not an integral part of the documentation user interface or documentation module. For example, in the case of radiology information, a radiology department may maintain its own database having radiological images and readings of numerous different patients stored thereon. Further, the radiology department may use a particular or specialized radiology application for accessing the radiology information stored on the radiology database. Consequently, when a user desires to access or view radiology information, the component launching module 110 initiates the particular radiology application as a launched component 112. Further, the component launching module 110 provides component specific context data 114 to the particular radiology application in an appropriate format and protocol used by the particular radiology application. The provision of the component-specific context data 114 enables the particular radiology application to directly access the relevant information for the patient that is the subject of the current document 106. Thus, the user is immediately presented with the patient's radiology information while still within the current document 106, and is able to easily access, cut and paste, or otherwise enter into the current document 106 desired radiology information obtained from the radiology application. Accordingly, implementations herein may apply component-specific context data 114 to launched components 112 for immediately accessing relevant patient information from various different databases throughout a health care institution, without requiring the user to separately open an application, provide authorization, and, for example, enter a patient's name, ID number, condition being treated, etc.

Furthermore, as discussed above, the framework 100 may include a message monitoring agent 116 that monitors both inbound data 118 and outbound data 120 for each launched component 112. For example, the inbound data 118 in general may include any data displayed by a launched component. The message monitoring agent 116 may capture the inbound data 118 based on various user actions, such as when a user copies a portion of the inbound data as a clipboard message 122.

The outbound data 120 may include a variety of messages and responses such as an HL7 message 124, a SOAP message 126, or an HTTP message 128 that are passed by the launched component 112 to a storage 130 that stores external data 132 for the launched component 112. For instance, an HL7 message 124 is a message that complies with the standards of the Health Level Seven (HL7) organization (e.g., HL7 v2.x, v3.0, HL7 RIM) for the exchange, integration, sharing, and retrieval of electronic health information. Additionally a SOAP message 126 (an acronym for Subjective, Objective, Assessment, and Plan) may contain a variety of information such as an entry by a health care provider in a patient's chart. Further, an HTTP (hypertext transfer protocol) message 128 is another example of a data type that may be passed by a launched component 112 to the storage 130.

As discussed above, storage 130 may be controlled by a remotely located server or other computing device, such as in another department of the health care institution, or the like. In other implementations, the storage 130 and external data 132 may be on the same computing device as the documentation system; however, the external data 132 is still external in the sense that the external data 132 was generated by an application that is external to the documentation system. For example, a user may use a dictation application on the user's own computing device to manage and store dictations and corresponding transcripts, and thus, the documentation framework may launch the dictation application as a launched component to view a dictation transcript relevant to the current document 106.

As mentioned above, portions of the inbound data 118 and the outbound data 120 may be captured by the message monitoring agent 116 and placed in a message queue 134. The message queue 134 may be accessed by a message rendering engine 136 which automatically renders rendering data 138 for updating the document 106 as data is added to the message queue. The rendering data 138 is used to update the rendered image of the current document 106 by updating the corresponding relevant information in the document 106.

Example System

Figure 2:
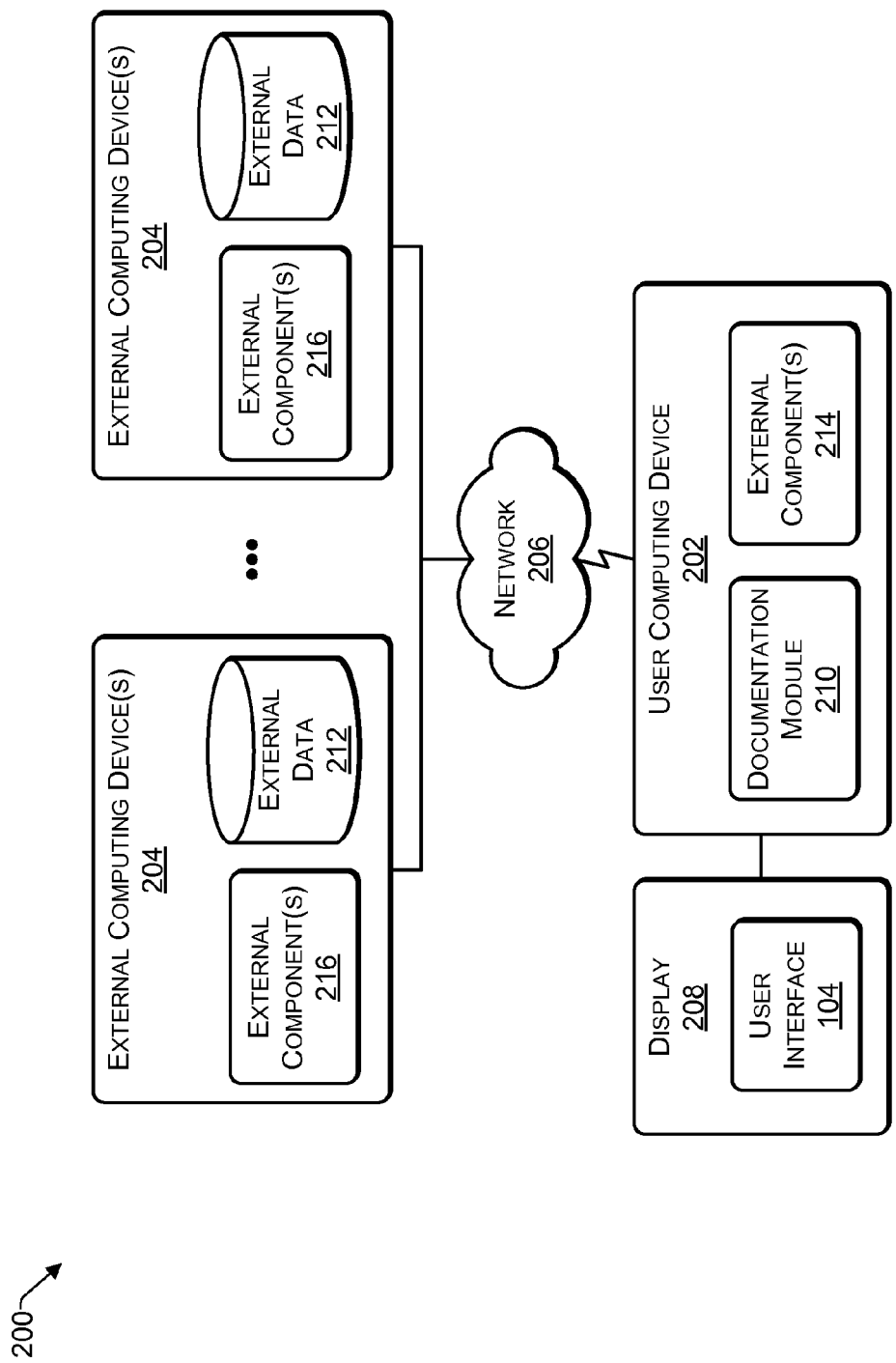
FIG. 2 is a block diagram of an example of a suitable system architecture for electronic documentation according to some implementations.

FIG. 2 illustrates an example architecture of a system 200 for generating and managing electronic documentation according to some implementations herein. To this end, the system 200 includes a user computing device 202 in communication with one or more external computing device(s) 204 through a network 206 or other communication link. User computing device 202 may be coupled to a display 208, and may include a documentation module 210 for implementing the framework 100 described above with respect to FIG. 1 and for displaying user interface 104 on display 208. In some implementations, user computing device 202 may be a personal computer, a workstation, a terminal, a mobile computing device, a PDA (personal digital assistant), a smartphone, a laptop, a tablet computing device, or other computing device having data processing capability. Documentation module 210 may communicate with external computing devices 204 over network 206 such as for obtaining external data 212 maintained by the external computing devices 204. In some implementations, documentation module 210 launches one or more external components 214 that are maintained on user computing device 202. For example, an external component 214 may be an application residing on user computing device 202 that accesses a particular database or a particular type of external data 212 maintained by external computing devices 204. Further, in some cases, the external data may be maintained on the user computing device 202, rather than maintained by an external computing device 204. In some implementations, documentation module 210 alternatively, or additionally, may launch one or more external components 216 maintained on external computing devices 216. For example, an external component 216 may be a network application, web service, or the like, that can be remotely accessed by user computing device 202 over network 206 for accessing external data 212 maintained by external computing device(s) 204. Other variations will also be apparent in view of the disclosure herein.

In some implementations, external computing devices 204 are server computing devices maintained by or for a health care institution, such as a hospital, hospital system, etc., and may be remotely located from the user computing device 202. For example, different departments and clinics of an institution may maintain separate external computing devices 204 for storing external data 212 relating to that department or clinic. In some implementations, external computing devices 204 may exist as a part of a data center, server farm, or the like, such as in an environment in which the data of a health care institution is managed off-site. In other implementations, the external computing devices 204 may be a combination of the two arrangements described above, or may be other types of server or storage computing devices that maintain information related to a patient or health care service. The system 200 can include any number of the external computing devices 204 in communication with any number of user computing devices 202. For example, in one implementation, network 206 includes the World Wide Web implemented on the Internet, including numerous databases, servers, personal computers (PCs), workstations, terminals, mobile devices and other computing devices spread throughout the world and able to communicate with one another. Alternatively, in another possible implementation, the network 206 can include as few as a single external computing device 204 in communication with one or more user devices 202 via a LAN (local area network) or a WAN (wide area network). Thus, the user computing device 202 can be coupled to the server computing device 204 in various combinations through a wired and/or wireless network 206, including a LAN, WAN, or any other networking technology, using one or more protocols, for example, a transmission control protocol running over Internet protocol (TCP/IP), or other suitable protocols. Furthermore, while an example system architecture is illustrated in FIG. 2, other suitable architectures may also be used, and implementations herein are not limited to any particular architecture.

Computing System Environment

Figure 3:
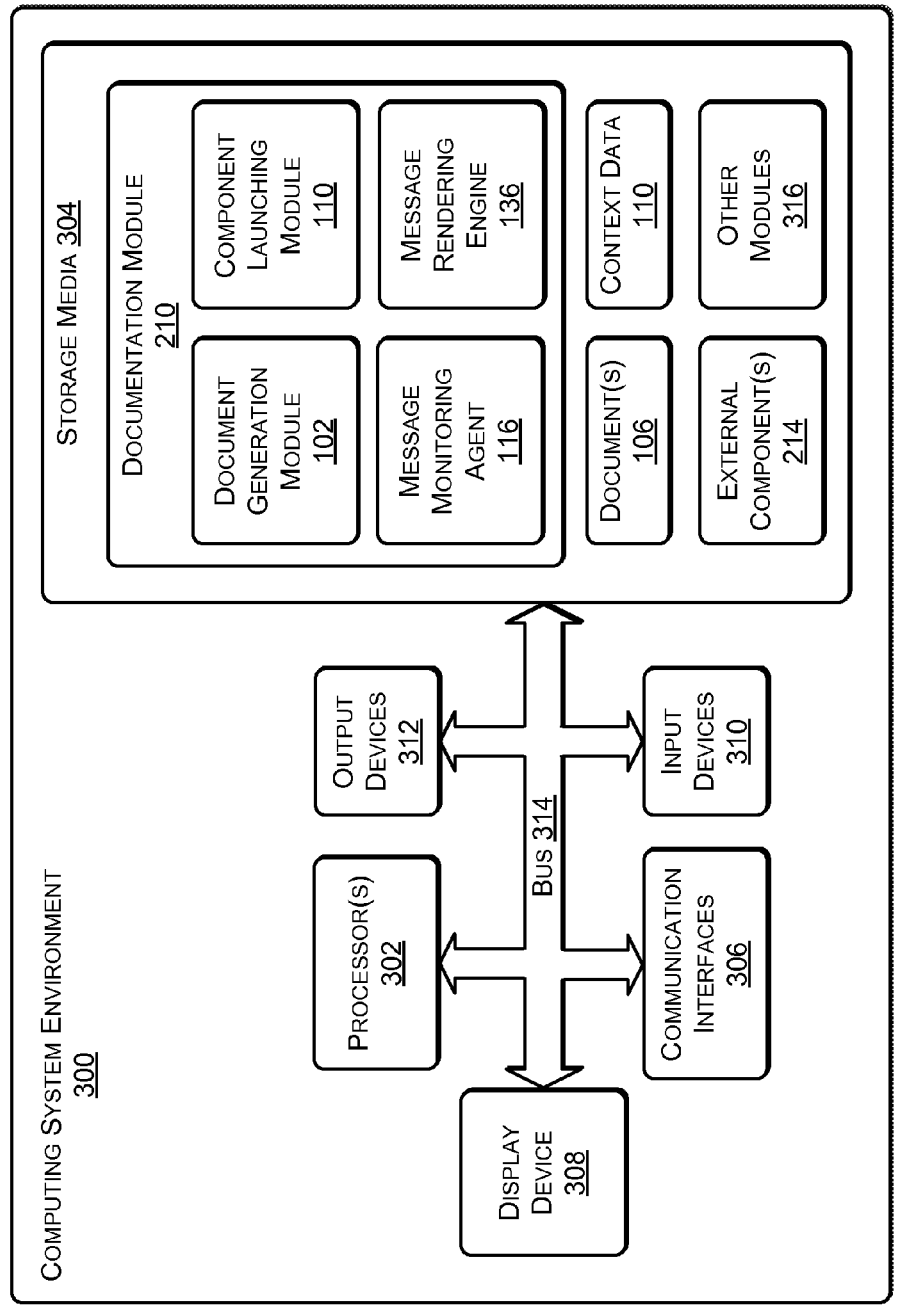
FIG. 3 is a block diagram of an example of a computing system environment for electronic documentation generation and management according to some implementations.

FIG. 3 illustrates an example configuration of a suitable computing system environment 300 according to some implementations herein. The computing system environment 300 may correspond to the user computing device 202 of FIG. 2 or other suitable device or system configured to implement the documentation management framework and techniques disclosed herein. Computing system environment 300 may include at least one processor 302, storage media 304, communication interfaces 306, a display device 308, input devices 310, and output devices 312, all able to communicate through a system bus 314 or other suitable connection.

The processor 302 may be a single processing unit or a number of processing units, all of which may include single or multiple computing units or multiple cores. The processor 302 can be implemented as one or more microprocessors, microcomputers, microcontrollers, digital signal processors, central processing units, state machines, logic circuitries, and/or any devices that manipulate signals based on operational instructions. Among other capabilities, the processor 302 can be configured to fetch and execute computer-readable instructions stored in the storage media 304.

Storage media 304 is an example of computer-readable storage media for storing instructions which are executed by the processor 302 to perform the various functions described herein. For example, storage media 304 may generally include memory and memory devices, such as both volatile memory and non-volatile memory (e.g., RAM, ROM, or the like). Further, storage media 304 may also include one or more mass storage devices, such as hard disk drives, solid-state drives, removable media, including external and removable drives, memory cards, Flash memory, floppy disks, optical disks (e.g., CD, DVD), storage arrays, storage area networks, network attached storage, or the like, or any combination thereof. Storage media 304 may be collectively referred to as memory or computer-readable storage media herein. Storage media 304 is capable of storing computer-readable, processor-executable program instructions as computer program code that can be executed on the processor 302 as a particular machine configured for carrying out the operations and functions described in the implementations herein.

Storage media 304 may maintain the documentation module 210, which can be executed on the processor 302 for implementing the documentation generation and management functions described herein. When implementing the framework 100 described above, documentation module 210 may include document generation module 102, component launching module 110, message monitoring agent 116, and message rendering engine 136. Storage media 304 may also include documents 106 created using documentation module 210, context data 110, and/or one or more external components 214, as discussed above with reference to FIGS. 1 and 2. Storage media 304 may further include other modules 316 such as an operating system, device drivers, communication software, and other applications.

The computing system environment 300 can also include one or more communication interfaces 306 for exchanging data with other devices, such as via a network, direct connection, and so forth. The communication interfaces 306 can facilitate communications within a wide variety of networks and protocol types, including wired networks (e.g., LAN, cable, etc.) and wireless networks (e.g., WLAN, cellular, satellite, etc.), the Internet and the like.

The display device 308, may be any know display device such as an LCD or CRT monitor, television, projector, touch screen, or other display. In addition input devices 310 may include devices such as a mouse, a keyboard, a camera, a microphone, a joystick, and so forth. Output devices 312 may include devices such as speakers, printers, and the like. Further, external computing devices 204 may include physical components similar to those described above with reference to the computing system environment 300.

The example environments, systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer-readable storage devices. Thus, the processes, components and modules described herein may be implemented by a computer program product.

Although illustrated in FIG. 3 as being stored in storage media 304 of computing system environment 300, documentation module 210, or portions thereof, may be implemented using any form of computer-readable media that is accessible by computing system environment 300. Computer-readable media may include, for example, computer storage media and communications media. Computer storage media, such as storage media 304, is configured to store data on a non-transitory tangible medium, while communications media is not.

As mentioned above, computer storage media includes volatile and non-volatile, removable and non-removable media implemented in any method or technology for storage of information, such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store information for access by a computing device.

In contrast, communication media may embody computer readable instructions, data structures, program modules, or other data in a modulated data signal, such as a carrier wave, or other transport mechanism.

Example Process

Figure 4:
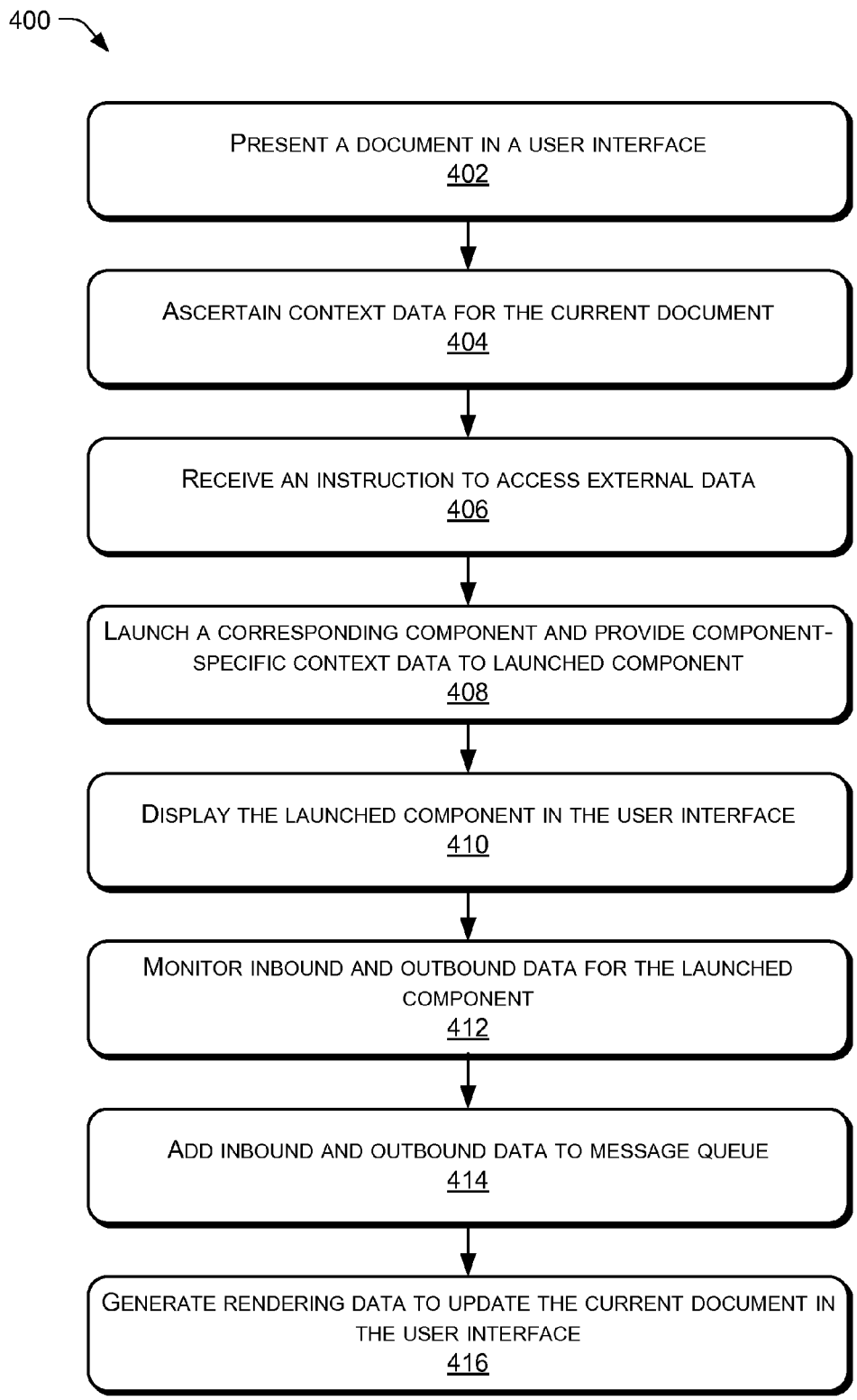
FIG. 4 is a flow diagram of an example process for electronic documentation generation and management according to some implementations herein.

FIG. 4 is a flow diagram of an example process 400 for electronic documentation according to some implementations herein. In the flow diagram, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, components, data structures, and the like that perform particular functions or implement particular abstract data types. The order in which the blocks are described is not intended to be construed as a limitation, and any number of the described operations can be combined in any order and/or in parallel to implement the process. For discussion purposes, the process 400 is described with reference to the framework 100 of FIG. 1 and the system 200 of FIG. 2, although other frameworks, devices, systems and environments may implement this process.

At block 402, the user interface presents a document for generating the document, such as for performing clinical documentation according to implementations herein. For example, a user may open a new document or may continue working on an existing document.

At block 404, the context data for the current document is determined. For example, as discussed above, the context data for the current document may include information such as the patient's name or other patient identifier; an illness, condition, symptoms, or diagnosis of the patient; a health care facility identification, such as a hospital, clinic and/or department treating the patient; a current date and time; a current location of the patient; a doctor's name or other identifier of a health care provider preparing the document and/or treating the patient; access privileges and authorization information of the person preparing the document; and so forth. The context data may be stored in conjunction with the document and associated with the document as metadata, or may be ascertained each time the document is opened.

At block 406, the user interface may receive an instruction to access external data. For example, as discussed additionally below, a user may enter a macro name, or select a macro from a list of available macros. The macro may be configured to provide commands and information for launching an external component for accessing the external data type that the user is interested in viewing or with which the user is interested in interacting.

At block 408, the component launching module is activated by the macro instructions to launch the corresponding external component and to further provide component-specific context data to the launched component. For example, a first component may use a first set of context parameters delivered in a first format for accessing the particular external data controlled by the first component, while a second component may use a second set of context parameters, different from the first set, and in a second format, for accessing particular data control by the second component. The component launching module is configured to automatically provide the suitable context parameters to each component in a format according to the specifications of the particular component.

At block 410, the launched component may be displayed in the user interface. For example, the launched component may be displayed in a separate window contemporaneously with the display of the current document. Thus the user may cut and paste information from the launched component, manually copy information from the launched component, or the like. Furthermore, the user may interact with the information in the launched component such as for updating the information, changing information, or the like. In addition, the user may choose to launch multiple external components in the user interface, such as in separate windows. For example, these multiple components may be launched sequentially or contemporaneously, and multiple different types of external data may be presented in the user interface and interacted with by the user independently or together.

At block 412, the message monitoring agent monitors inbound and outbound messages to and from the launched component. For example, actions by the user may trigger an inbound message such as a "copy to clipboard" action. Content may also be obtained from a launched component through messages written by the external component back to the external computing device where the relevant external data is stored. Consequently, a user may cause an open component to trigger out various outbound messages, some of which may include information to be added to the current document.

At block 414, the monitoring agent may intercept any inbound or outbound data into a message queue for the message rendering engine 136. For example, when the user has finished reviewing or updating information in a launched component and submitted or saved any changes, the documentation framework herein may update the message queue with latest change. Additionally, the document is updated with any inbound data that was copied to a clipboard and pasted into the document.

At block 416, the message rendering engine generates rendering data to update the current document view in the user interface based upon the messages in the message queue. For example, a cut-and-paste action by the user causes the message rendering engine to render a new configuration for the current document that includes the pasted data. Furthermore, captured outbound messages may also be used to update portions of the document to which the outbound data pertains. For example, if the user employs a launched component to update HL7 information, SOAP information, or other information that forms part of the current document that was taken from a launched component, the message containing the updated information may be captured in the message queue and the updated information rendered in the document. Thus, if the user causes the external component to modify or update data during use of the external component, messages containing the modified or updated data can be automatically placed in the message queue and provided to the rendering engine for inclusion in the current document. Further, in some implementations, the rendering engine may render the result and place the result into the current documentation at an appropriate location, so that the latest information may be included in the current document. Implementations herein may also leverage Extensible Stylesheet Language Transformations (XSLT)/parsing language for dynamic rendering of a current document that a user is composing.

Example User Interface

Figure 5:
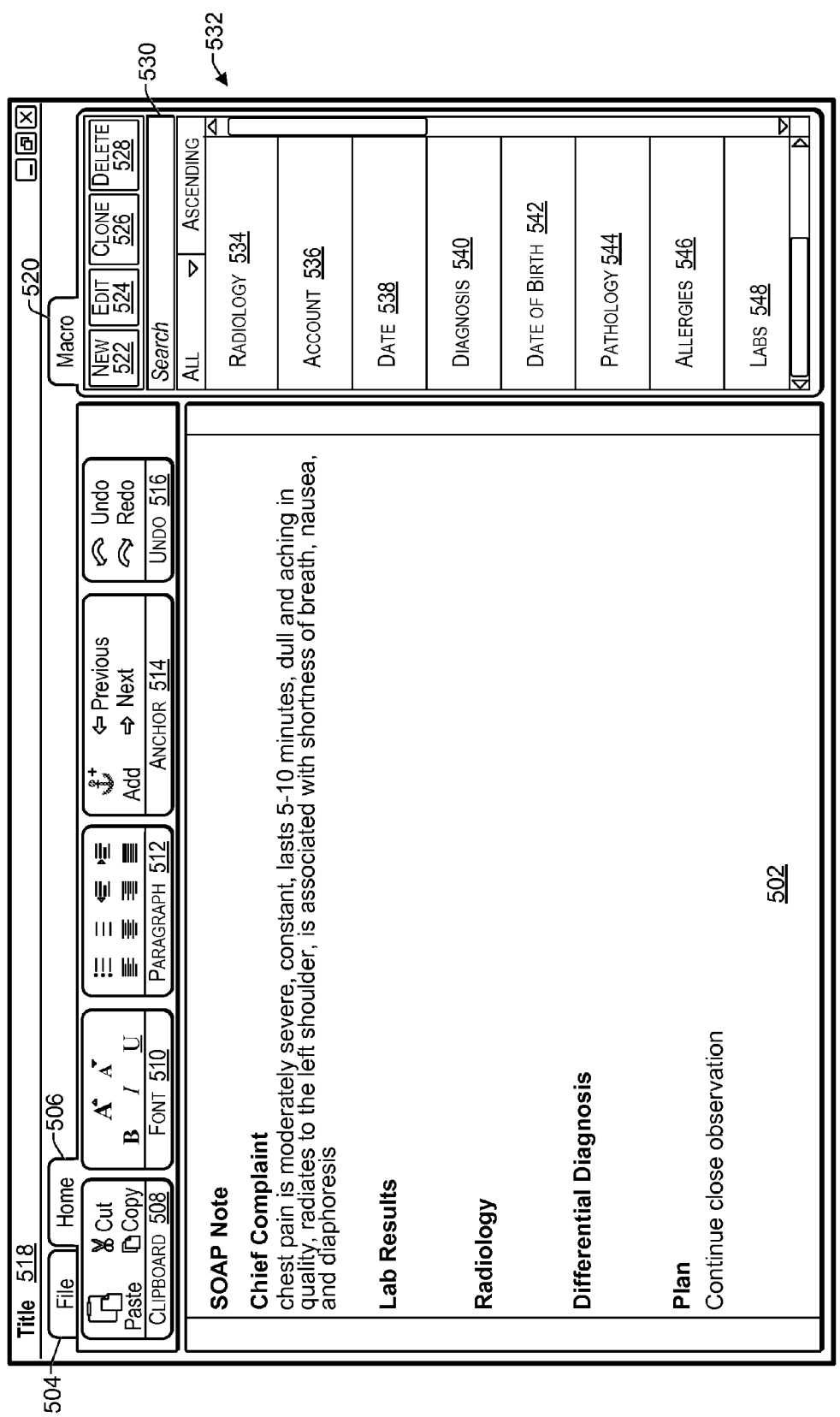
FIG. 5 is an example user interface for electronic documentation generation and management according to some implementations.

FIG. 5 illustrates an example of a user interface 500 for generating and managing electronic documentation according to some implementations herein. User interface 500 may include a variety of features useful for generating a document 502, such as a file tab 504, a home tab 506, clipboard controls 508, font controls 510, paragraph style controls 512, anchor controls 514, undo/redo controls 516, and a title 518, to name a few. Furthermore, user interface 500 may include a macro window 520 to facilitate creating and utilizing macros for launching various external components in the user interface 500. For example, macro window 520 may include controls for creating, editing, cloning and deleting macros, as illustrated by new button 522, edit button 524, clone button 526, and delete button 528, respectively. Macro window 520 may also include a search area 530, which the user may employ to locate a particular macro. Additionally, macro window 520 may include a list 532 of available macros that the user may refer to and click on for selecting a particular macro for launching a desired external component. Examples of macros that might be used in the environment of medical documentation include radiology 534, account 536, date 538, diagnosis 540, date of birth 542, pathology 544, allergies 546, and labs 548, to name a few. For example, radiology 534 may be used to launch a component for accessing radiology information; account 536 may be used to launch a component for accessing the patient's account and billing information; date 538 may be used to insert the current date; diagnosis 540 may be used to access a component to view or enter a diagnosis of the patient such as in a SOAP note or HL7 document; date of birth 542 may be used to insert the date of birth of the patient; pathology 544 may be used to launch a component to access and review the pathology reports for the patient corresponding to the current document; allergies 546 may be used to launch a component that provides information on the allergies of the patient; and Labs 548 may be used to launch a component that accesses and displays any lab reports for the patient. Furthermore, while several macros are shown in the list 532 numerous other macros may also be provided in the list 532 and may be scrollable or otherwise accessible by a user of the interface 500.

Information Insertion Example

Figure 6:
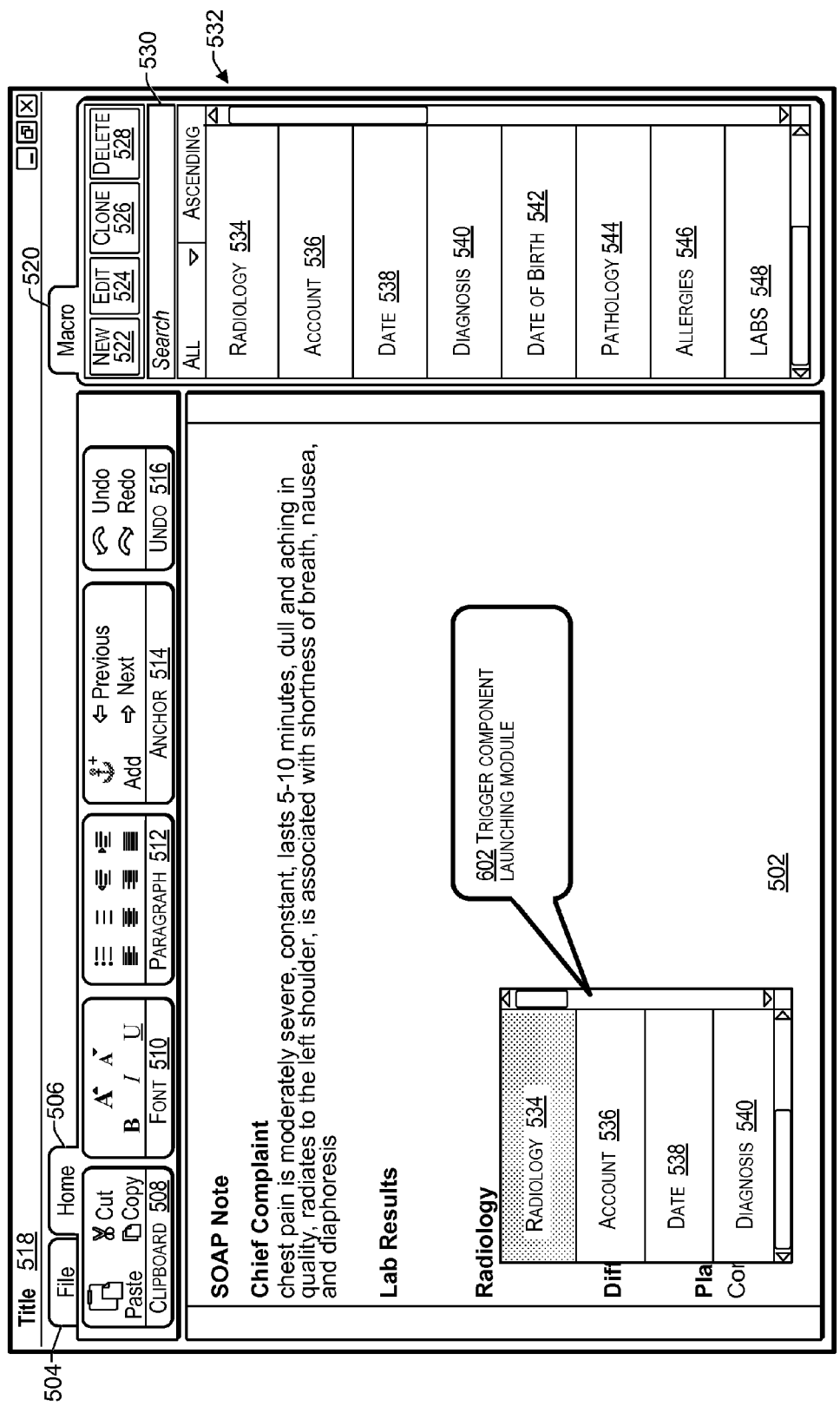
FIG. 6 is an example user interface illustrating triggering the component launching module.

FIGS. 6-10 illustrate example operations carried out in the user interface 500 for launching a component and adding information from the component to the document 502 being generated. For example, in the current document 502 the user has already included information regarding the "Chief Complaint" and the "Plan" for the patient. Suppose that the user now wishes to add radiology information to the document 502. As illustrated in FIG. 6, at block 602, the user employs a macro to trigger the component-launching module 110. The macro to trigger the component-launching module 110 may be activated in several different ways, such as by using a right click and selecting the radiology macro 534 as is illustrated. Alternatively, the user may type in the name of the radiology macro, e.g., "\rad". Still alternatively, the user may click on the radiology macro 534 in the list of macros 532.

Figure 7:
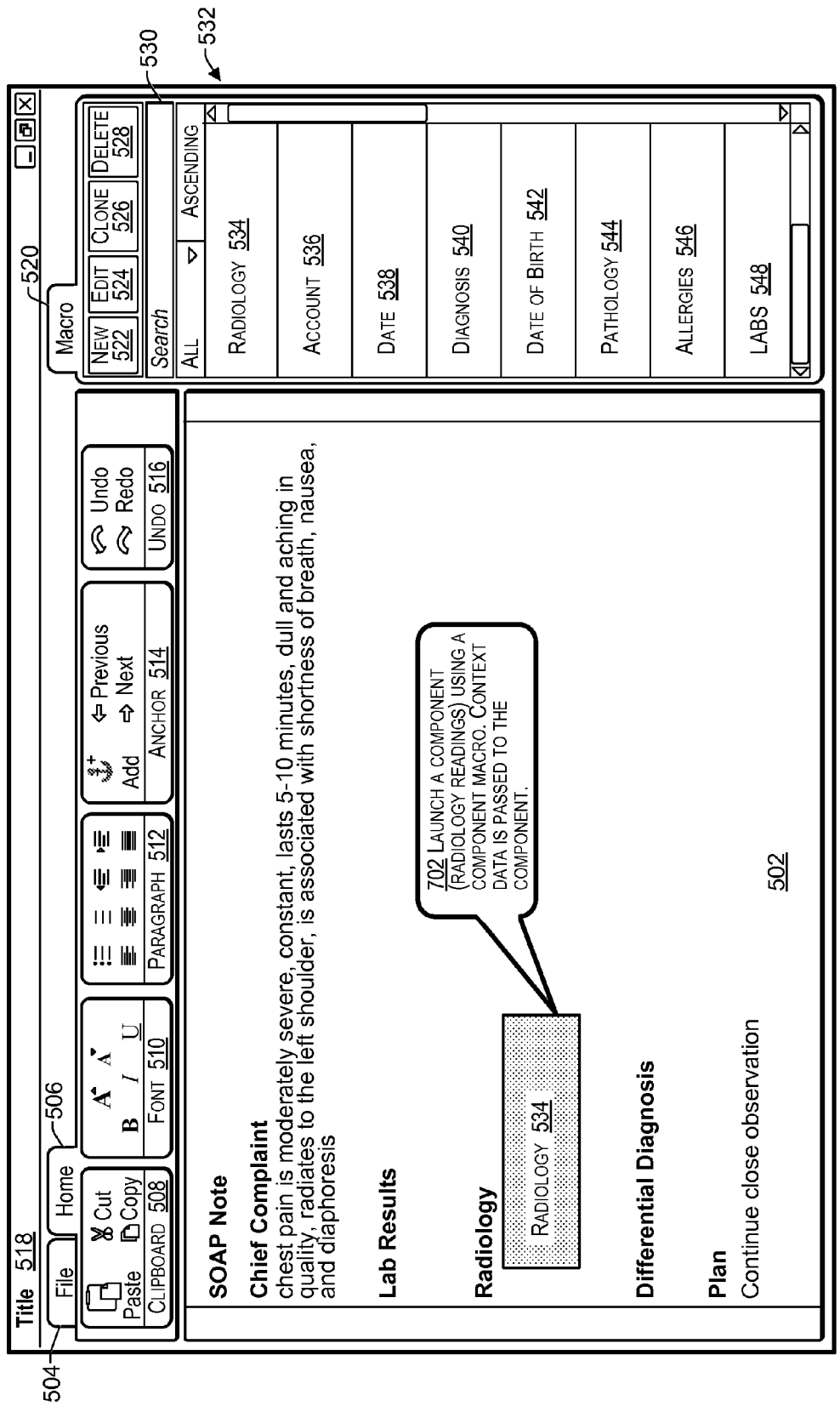
FIG. 7 is an example user interface illustrating launching a component using a component macro.

As illustrated in FIG. 7, at block 702, through the user's selection of the radiology macro 534, the component launching module 110 launches a radiology component, which may be a third-party application for accessing radiology readings. As discussed above, the context data for the current document 502 is passed to the radiology component so that the radiology component automatically accesses and displays the correct information corresponding to the patient that is the subject of the current document 502.

Figure 8:
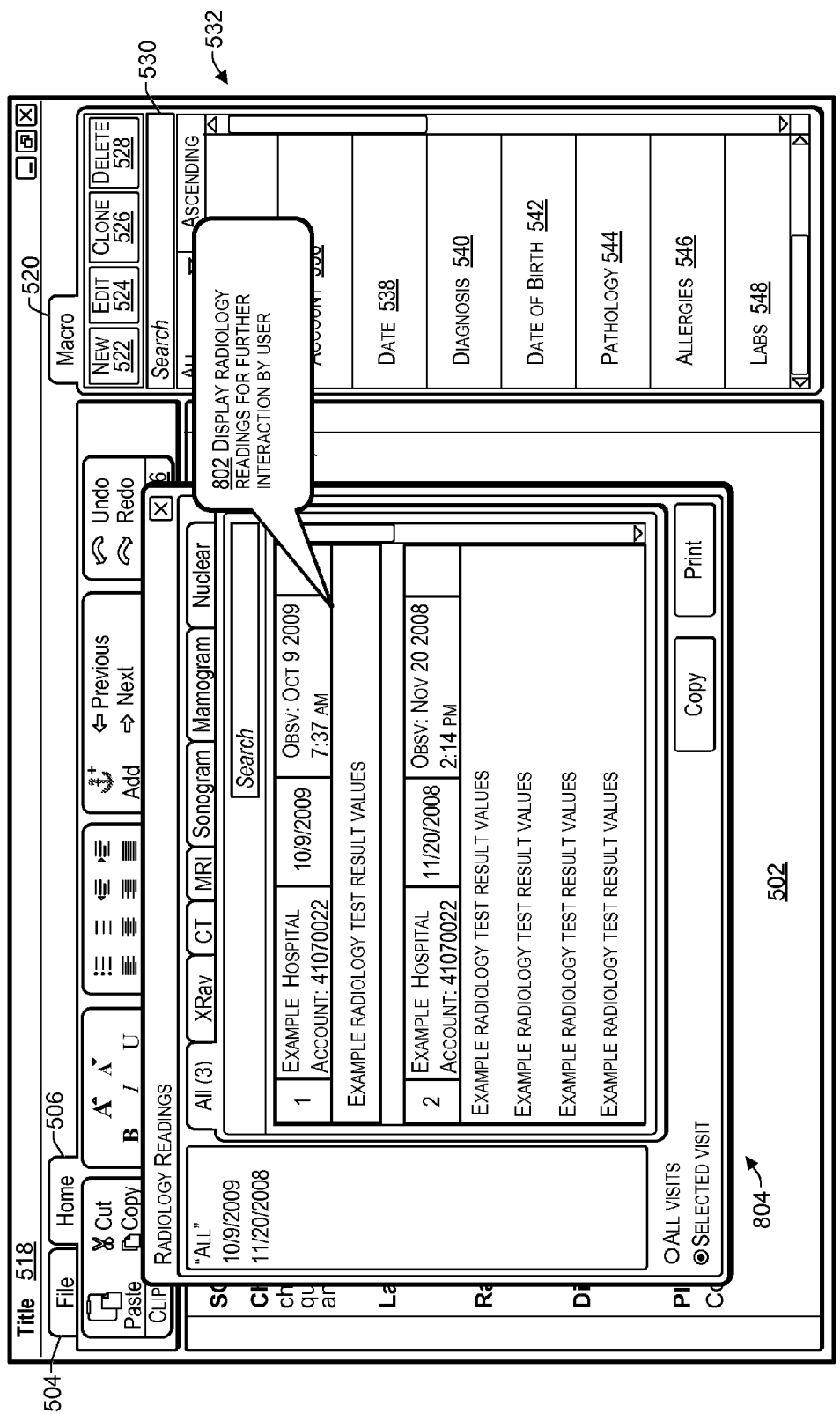
FIG. 8 is an example user interface illustrating display of a component within the user interface.

As illustrated in FIG. 8, at block 802 the launching of the radiology component results in display of the radiology readings 804 for the particular patient that is the subject of the current document 502. The radiology readings 804 are displayed contemporaneously with the display of the current document 502 to enable the user to enter desired information from the radiology readings 804 into the current document 502.

Figure 9:
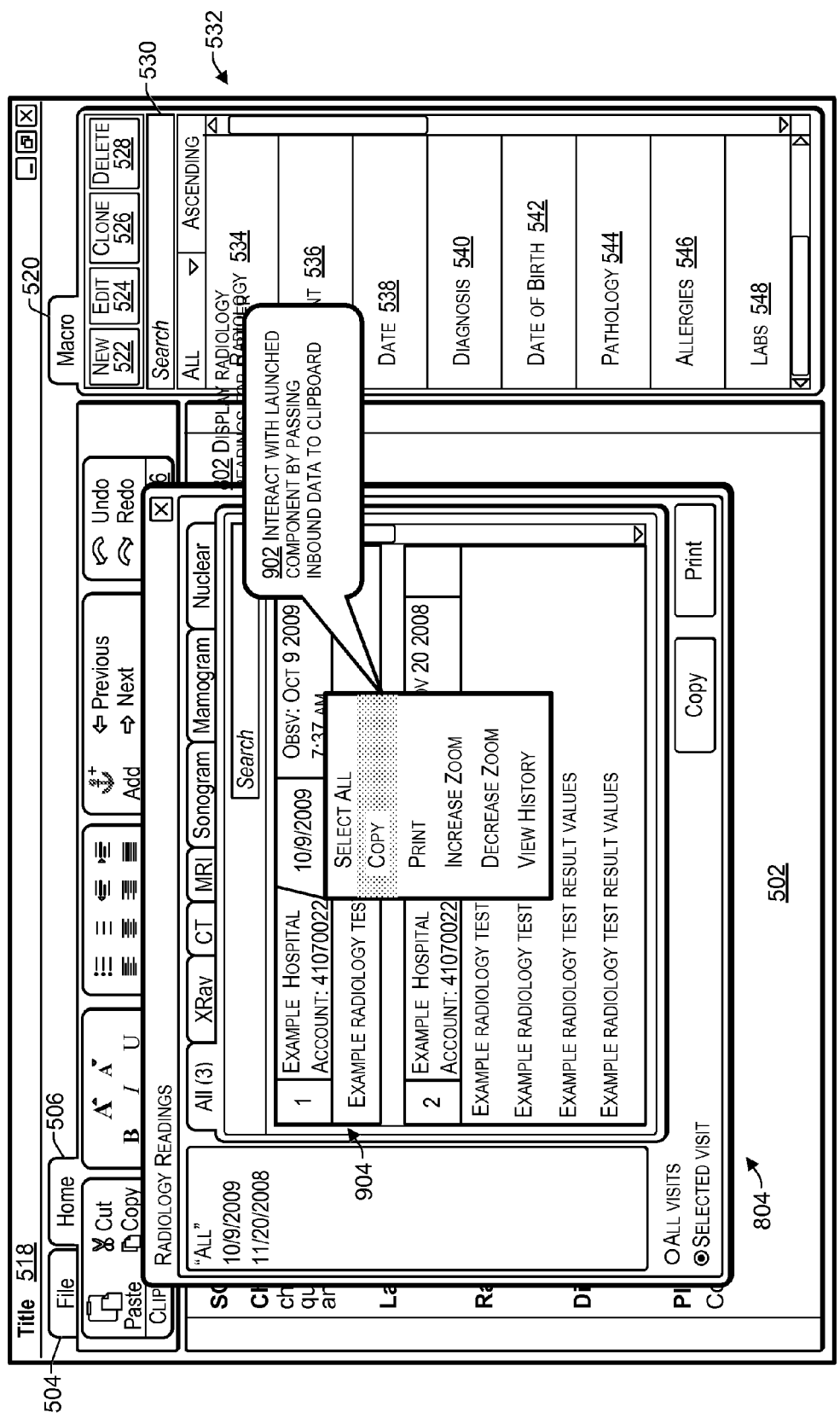
FIG. 9 is an example user interface illustrating interacting with a launched component.
Figure 10:
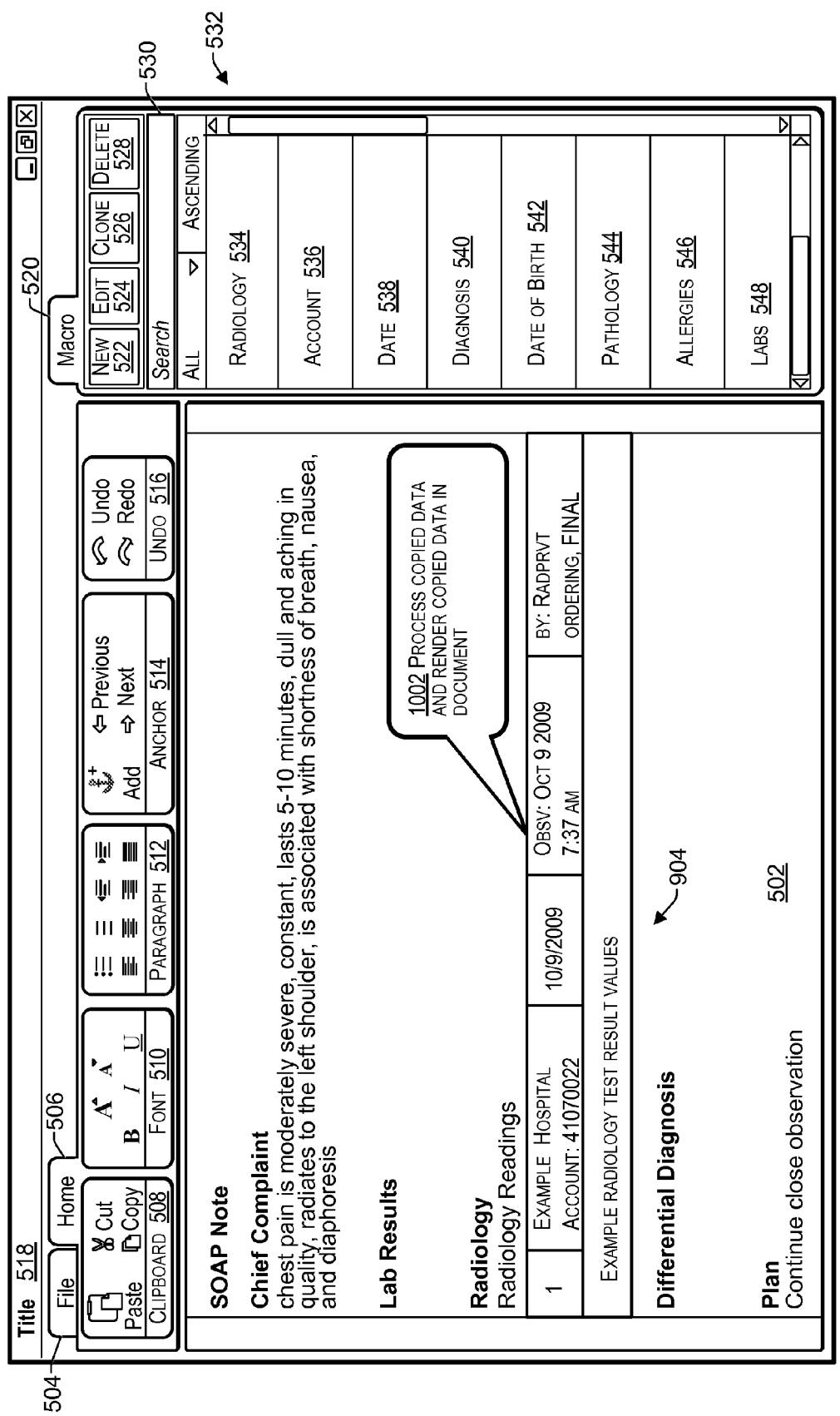
FIG. 10 is an example user interface illustrating rendering data into the document.

As illustrated in FIG. 9, at block 902, the user interacts with the launched radiology component, such as by copying information 904 contained in the displayed radiology component. The copied information 904 is captured as inbound data to the clipboard and placed in the messaging queue 134, as described above. As illustrated in FIG. 10, at block 1002, upon detection of a paste function carried out by the user, the copied information 904 is rendered in the current document 502, by the rendering engine 136, at a location indicated by the user, as described above.

Macro Creation Example

Figure 11:
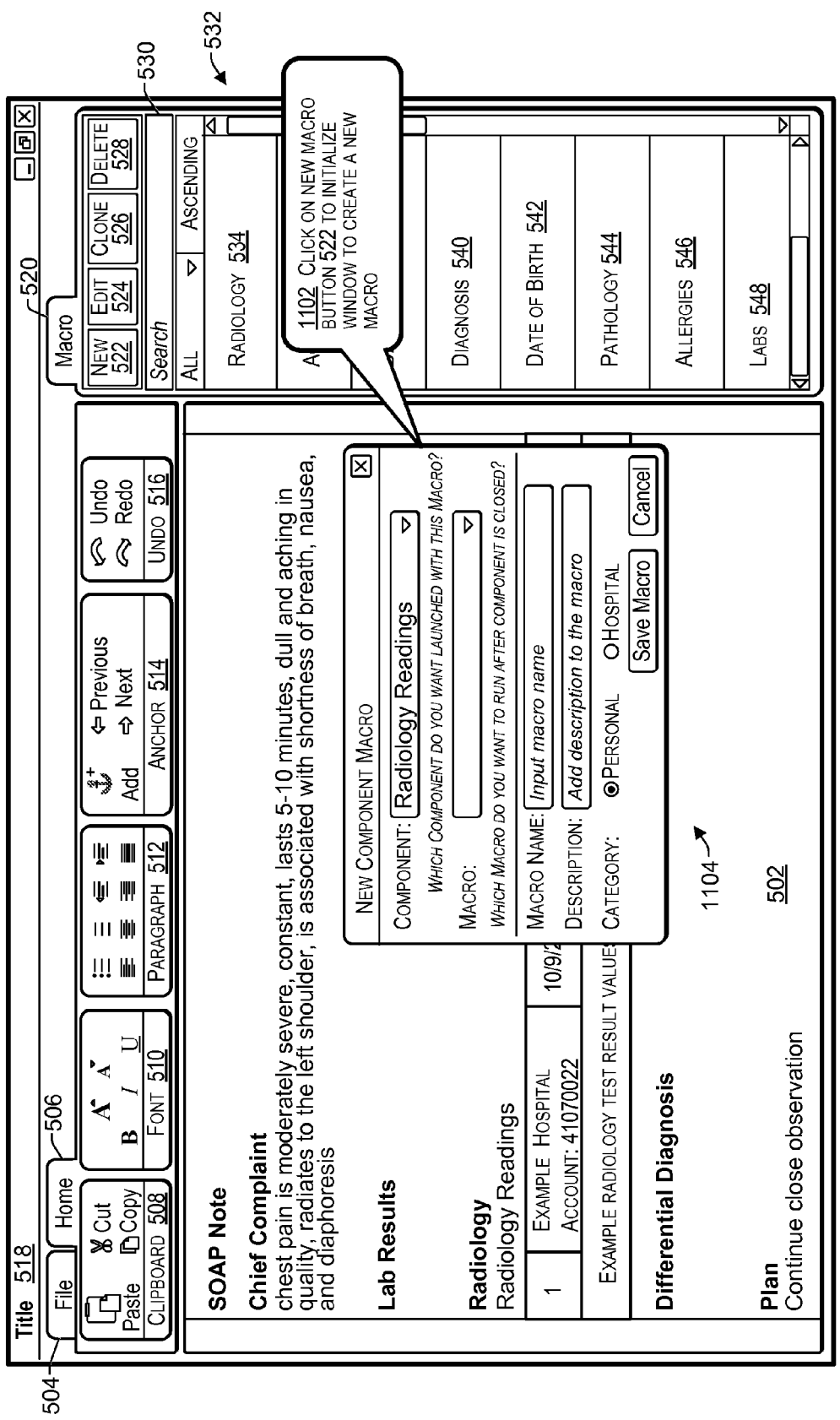
FIG. 11 is an example user interface illustrating initializing a window to create a new macro.
Figure 12:
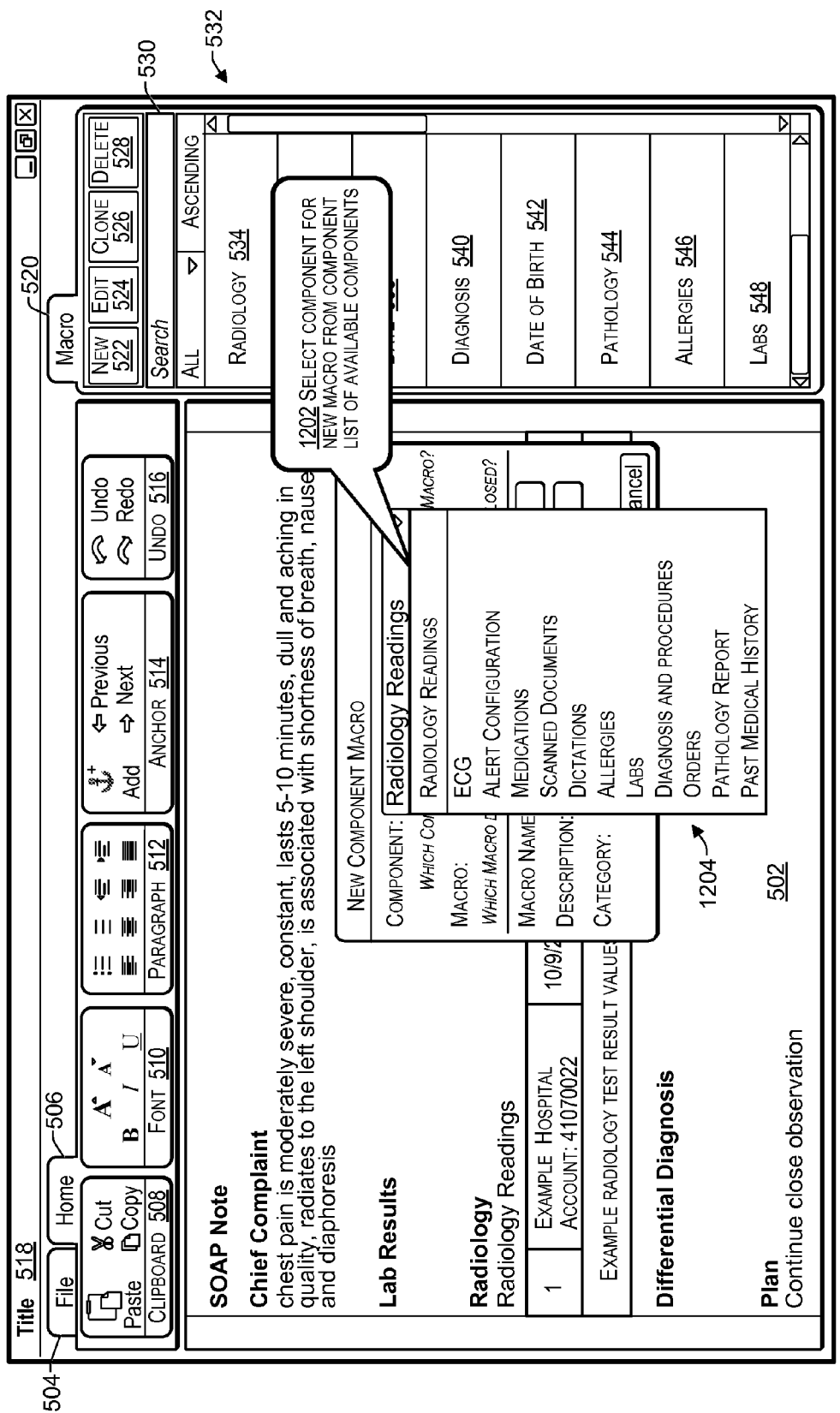
FIG. 12 is an example user interface illustrating selecting a component for the new macro.

FIGS. 11-14 illustrate example operations carried out in the user interface 500 for creating a new component macro. For example, suppose that the radiology component described above with reference to FIGS. 6-10 did not yet have a macro configured for launching the radiology component. As illustrated in FIG. 11, at block 1102, the user may click on the new macro button 522 to initialize a new component macro window 1104. As illustrated in FIG. 12, at block 1202, the user may select the component for the new macro from a list of available components 1204. For example, the documentation module 210 may determine which components 214 are available on the user computing device 202, or available on external computing devices 204, for interaction with the documentation module 210. The documentation module 210 may also include any new components in the list of available components 1204. In a medical documentation setting, typical components may include a radiology component, an electrocardiogram component, an alert configuration component, a medications component, a scanned documents component, a dictations component, an allergies components, a labs component, a diagnosis & procedures component, an orders component, a pathology reports component, a past medical history component, a charts component, a demographic component, and an accounts component, to name a few examples.

Figure 13:
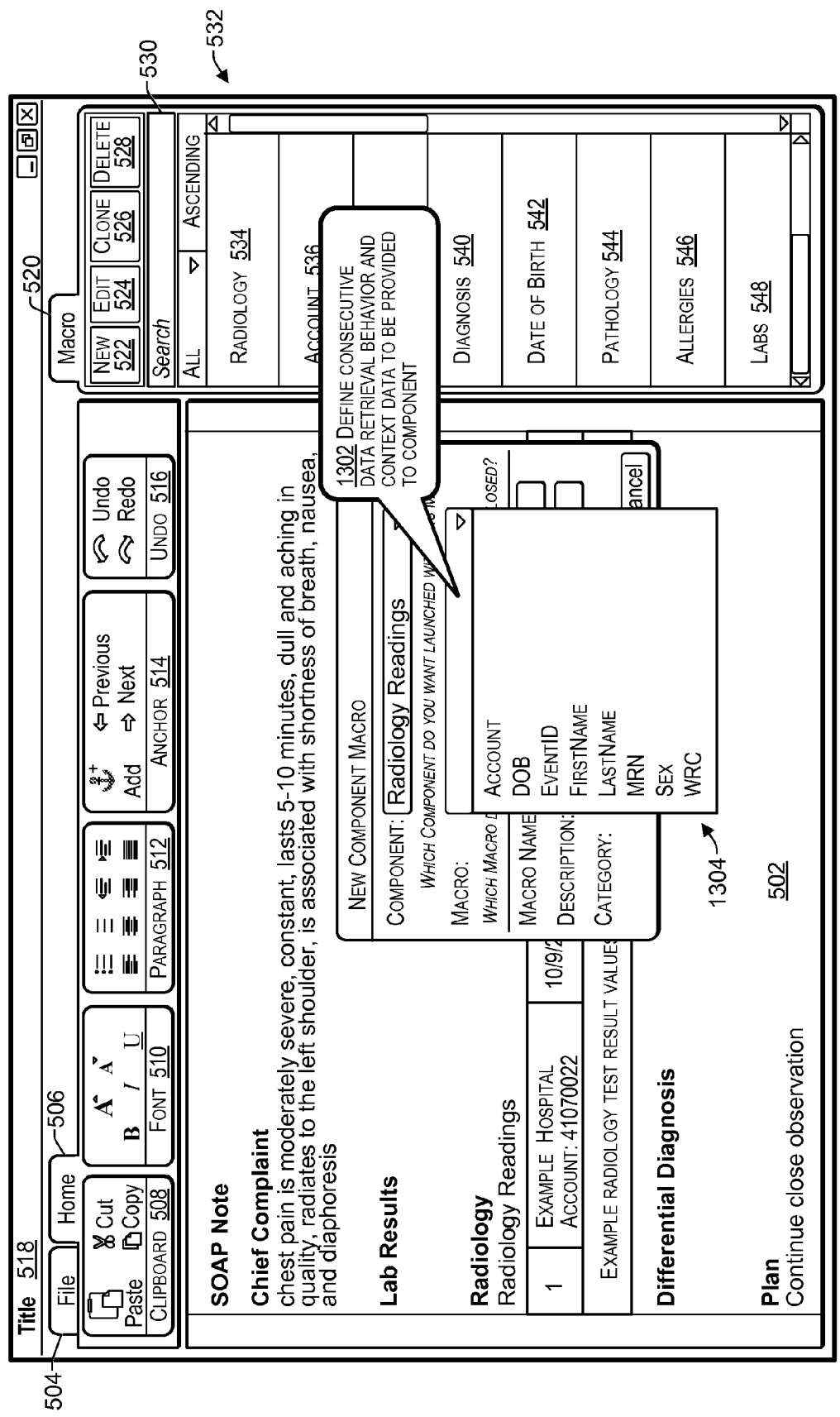
FIG. 13 is an example user interface illustrating defining data retrieval behavior for the new macro.
Figure 14:
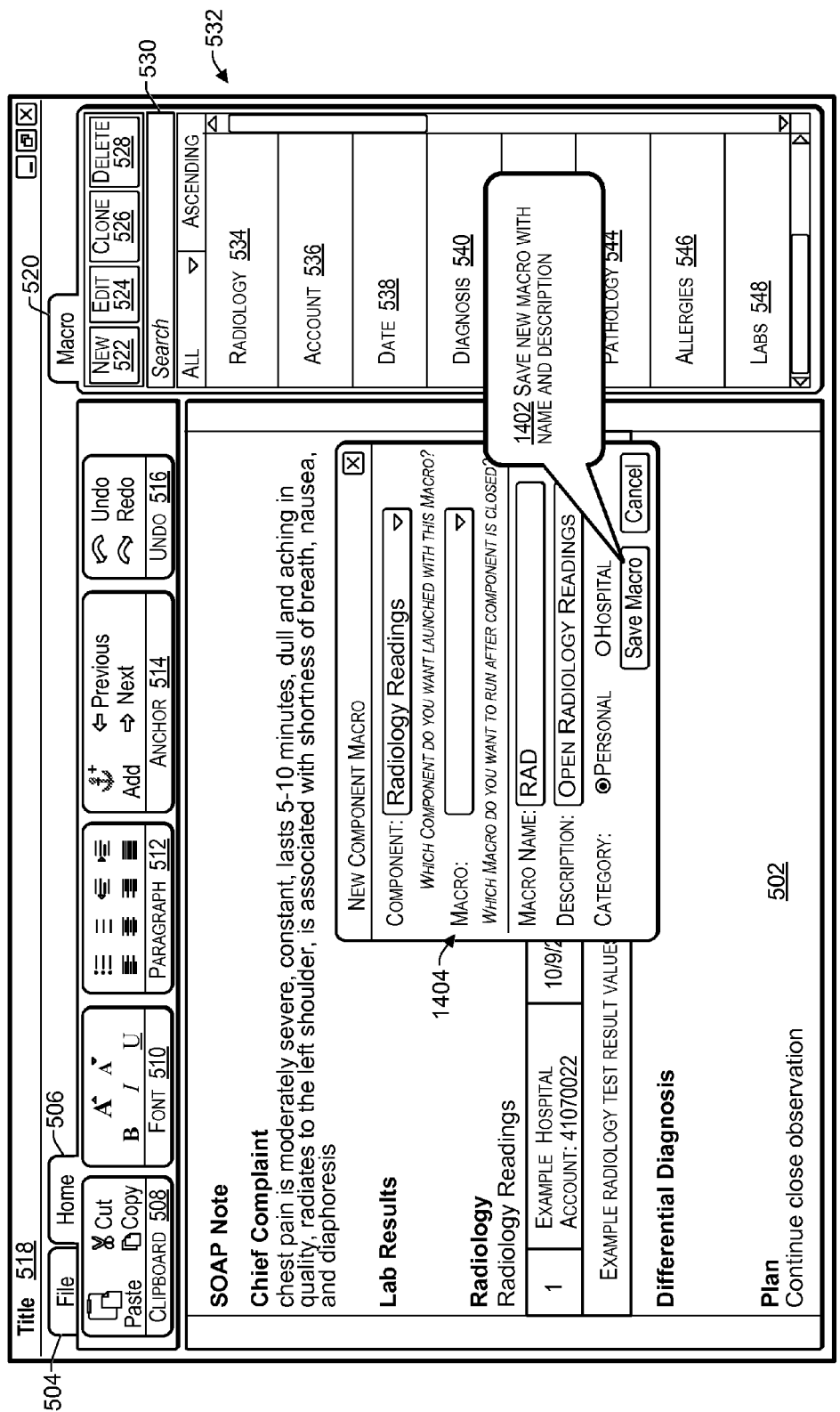
FIG. 14 is an example user interface illustrating saving the new macro with a name and description.

As illustrated in FIG. 13, at block 1302, the user may define consecutive data retrieval behavior 1304 to be performed by the component when the macro is initiated and may further define context data, format, etc., to be provided to the component when the macro is initiated. As illustrated in FIG. 14, at block 1402, when the user has completed defining the behavior of the new macro for launching the component, the user may save the new macro with a macro name and description 1404. Existing macros may be edited or cloned using a similar technique to that described above with reference to FIGS. 11-14.

Structured Data Input Example

Figure 15:
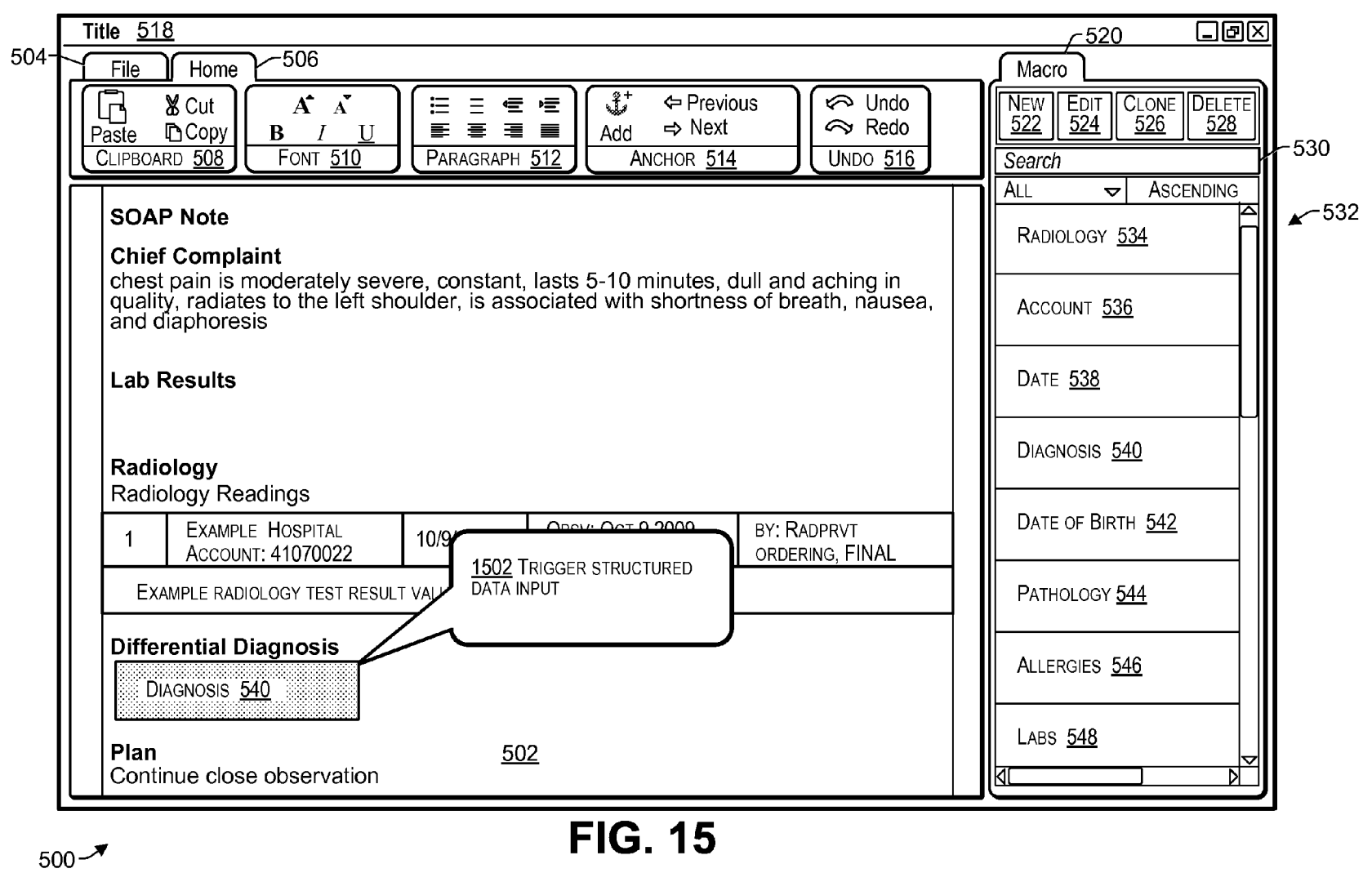
Figure 16:
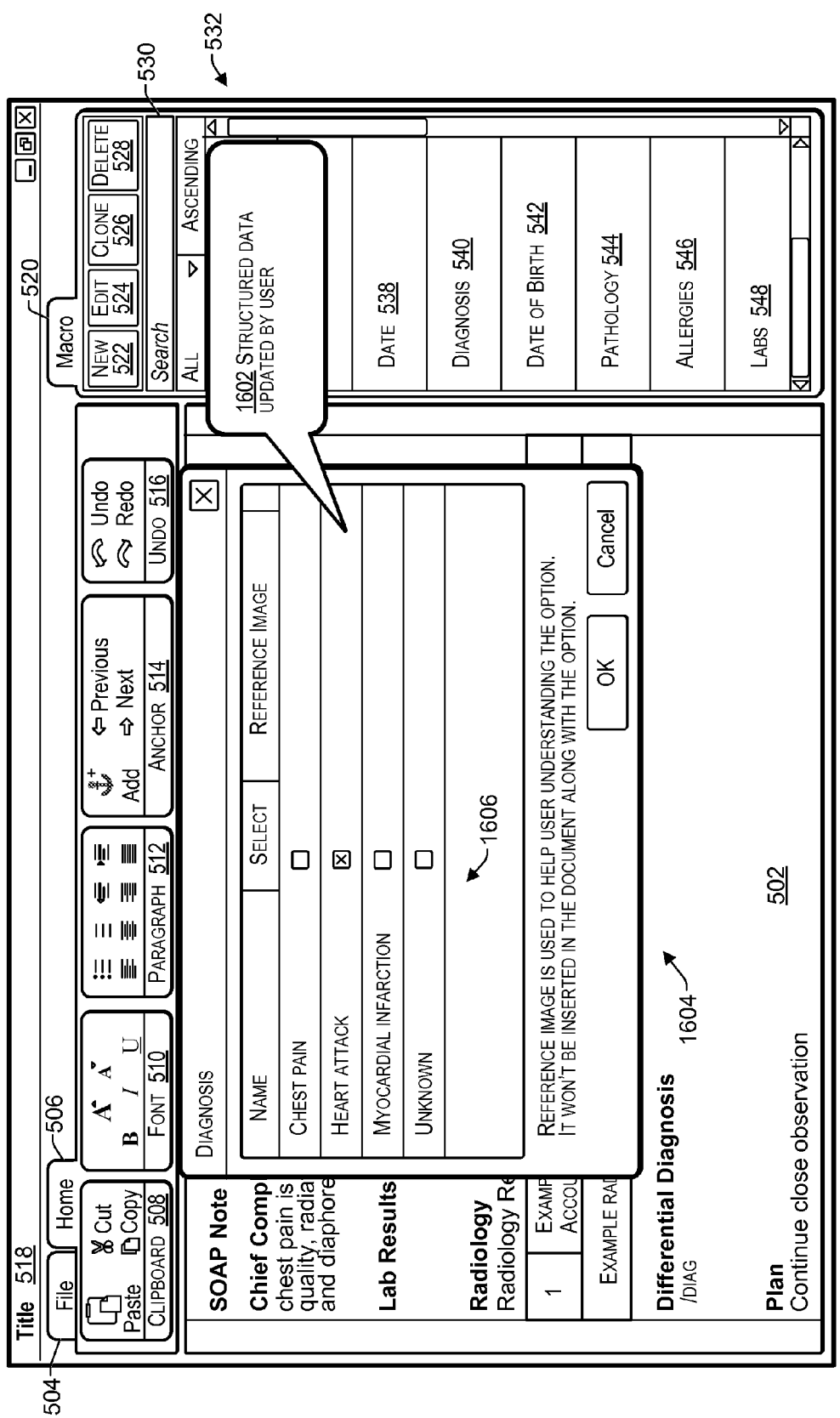
FIG. 16 is an example user interface illustrating structured data updated by the user.

FIGS. 15-17 illustrate example operations carried out in the user interface 500 for structured data input. For example, as illustrated in FIG. 15, at block 1502, the user may trigger structured data input in the current document 502, such as under "Differential Diagnosis" by initializing the diagnosis macro 540. As illustrated in FIG. 16, at block 1602, the triggering of the diagnosis macro 540 results in the component launching module 110 launching a diagnosis component 1604 that includes a list of possible diagnoses 1606 for the current patient. Thus, the user is able to select a diagnosis from the list of possible diagnoses 1606. As illustrated at FIG. 17, at block 1702, the selected diagnosis (i.e., myocardial infarction) is rendered into the document 502 under the "Differential Diagnosis" heading using structured terminology, which may, for example, conform to SNOMED CTS terminology.

Outbound Data Input Example

Figure 18:
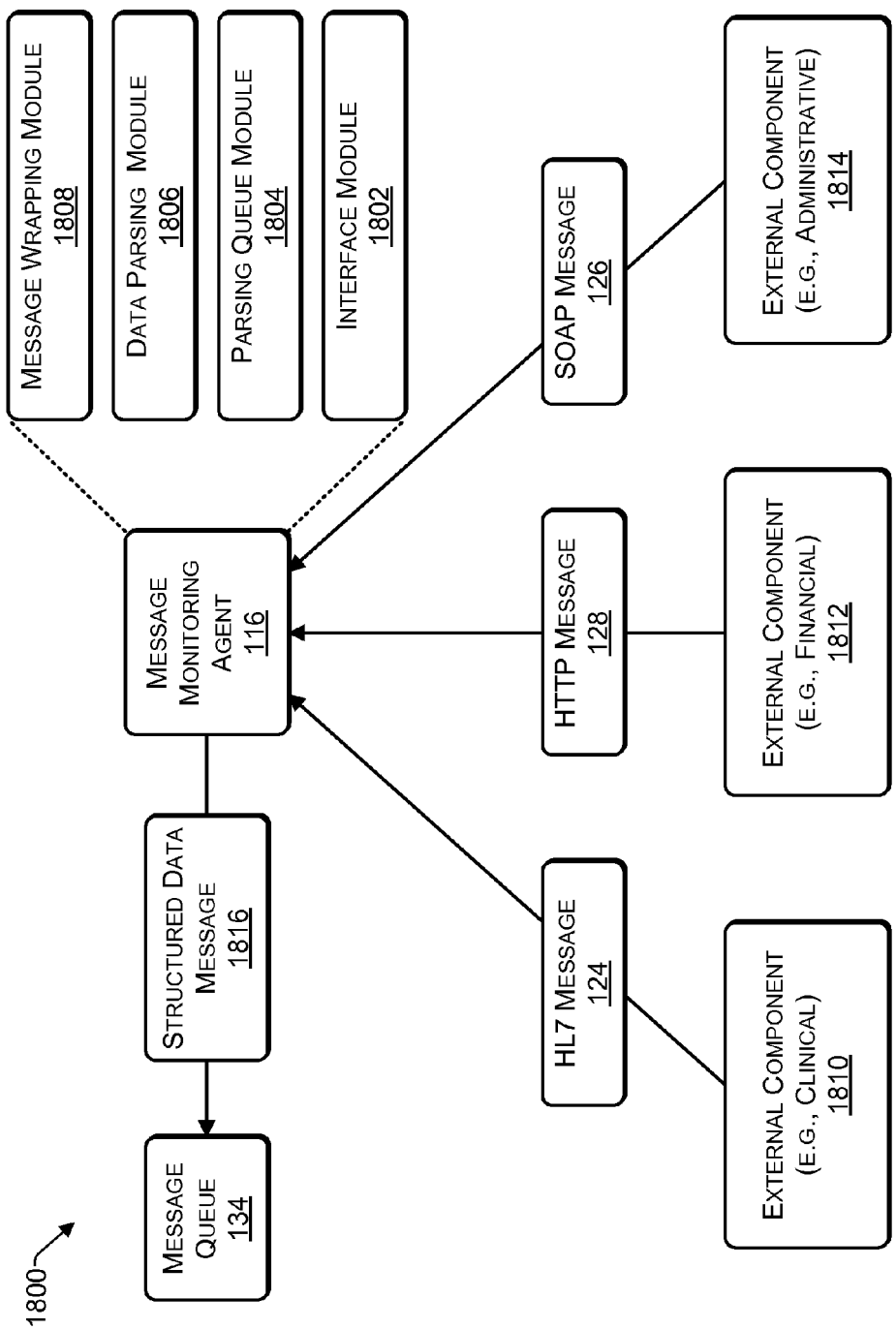
FIG. 18 is block diagram of an example framework for capturing outbound data triggered by the user.

FIG. 18 is a block diagram of an example framework 1800 for capturing outbound data from an external component for inclusion in a document according to some implementations. Monitoring agent 116 may include an interface module 1802, a parsing queue module 1804, a data parsing module 1806, and a message wrapping module 1808. Interface module 1802 may be configured to intercept outbound messages, such as may be sent from an external module to storage or other recipient, as described above. For example, a user may perform an action or operation to cause an external module to generate and send a message. Thus, as non-limiting examples, an external component 1810, such as a clinical component, may send an HL7 message 124, such as latest lab results, a medication update, or the like. Further, an external component 1812, such as a financial component, may send an HTTP message 128, such as an update to a patient's financial data. Additionally, an external component 1814, such as an administrative component, may send a SOAP message 126, such as to change a treatment plan. The interface module 1802 intercepts these messages and provides the intercepted messages to the parsing queue module 1804, which queues the intercepted messages for parsing.

The data parsing module 1806 parses the captured messages to identify any information contained in the captured messages that may be relevant to the current document or that was requested for the current document. For example, if medication was changed or updated through use of an external component, the medication change may be captured and identified for updating in the current document. Further, if a lab result is triggered from an external component, the latest lab result may be captured and identified for updating in the current document. Following data parsing, the data identified for inclusion in the current document is provided to the message wrapping module 1808. The message wrapping module 1808 outputs the identified data as a structured data message 1816. The message wrapping module 1808 provides the structured data message 1816 to the message queue 134 for rendering in the current document, as described above.

Figure 19:
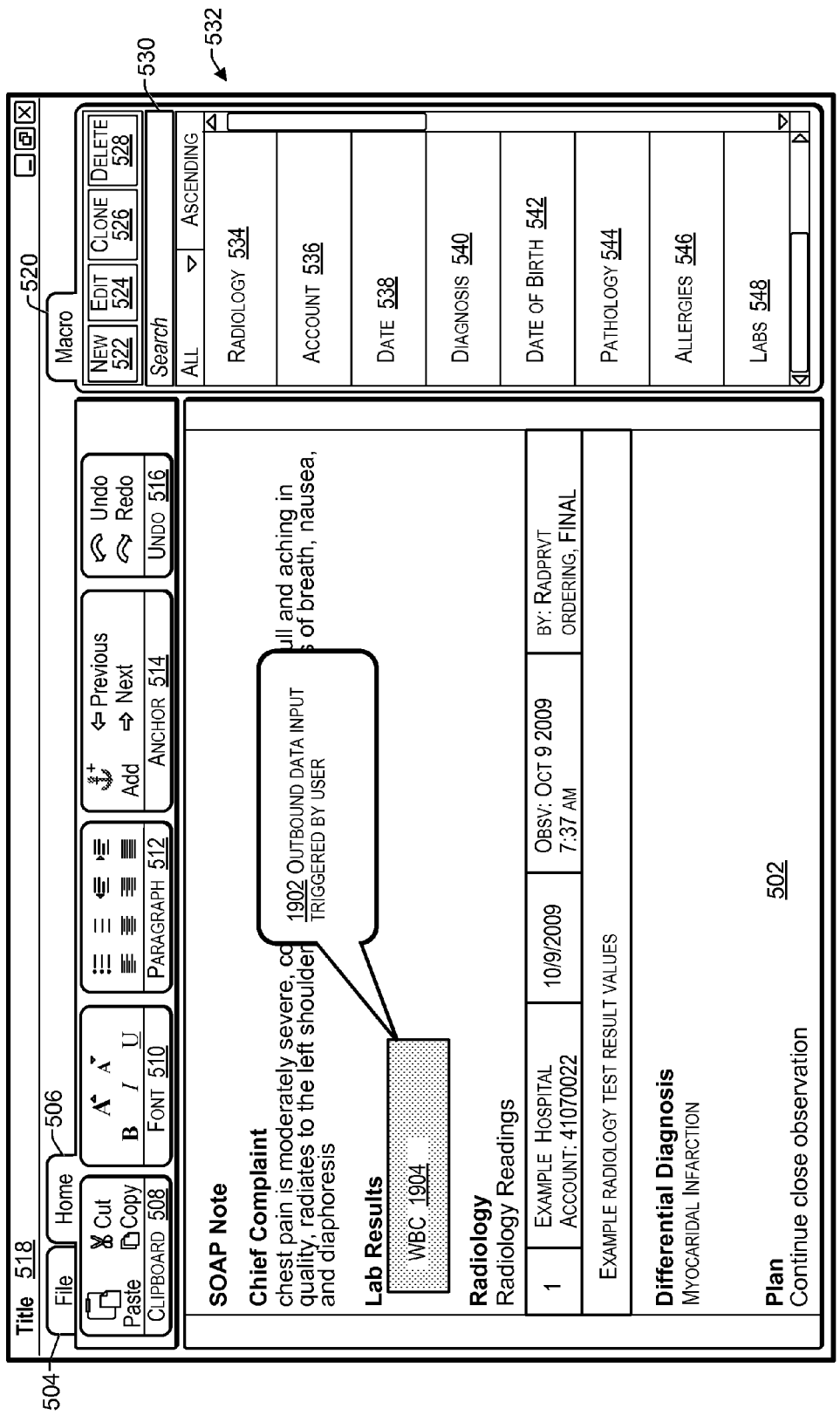
FIG. 19 is an example user interface illustrating outbound data input triggered by the user.
Figure 20:
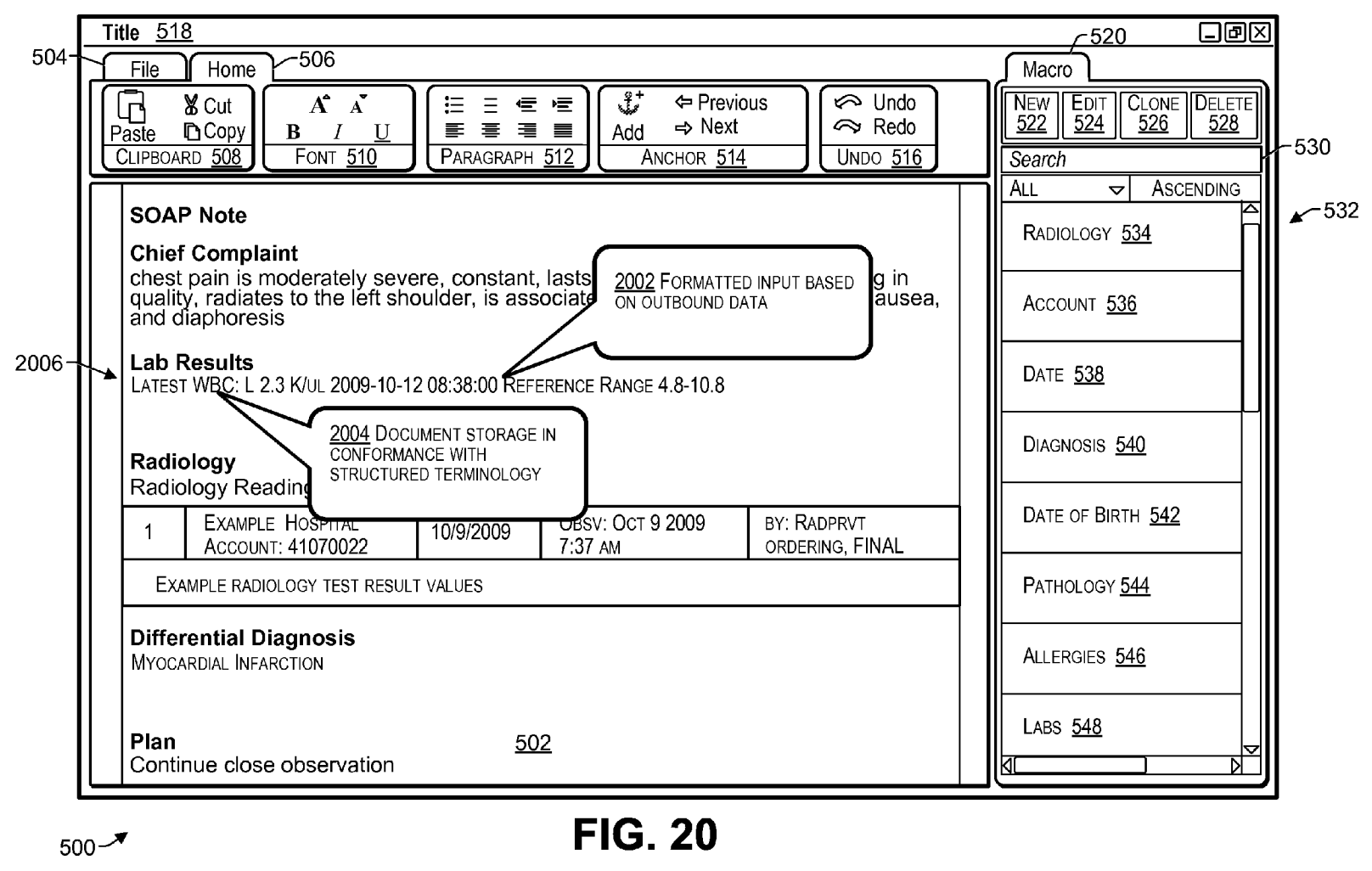

FIGS. 19-20 illustrate example operations carried out in the user interface 500 for outbound data input. For example, as illustrated in FIG. 19, in the current document 502, under "Lab results," at block 1902, the user may trigger a WBC (white blood cell count) macro 1904 to launch a labs component for determining the patient's white blood cell count. As illustrated in FIG. 20, the launched labs component is configured to send an outbound data message in response to a user trigger or action. The outbound data message may include the latest white blood cell count readings for the particular patient. For example, as described above, the outbound data message may be an HL7 message, a SOAP message, an HTML message, or the like. At block 2002, the outbound data message is captured by the message monitoring agent 116, as described above, and a corresponding structured data message 1816 is placed in the message queue 134. The structured data message 1816 is subsequently rendered into the current document 502 by the message rendering engine 136. Further, at block 2004, the white blood cell count data 2006 that is rendered in the current document 502 may be structured in conformance with structured terminology, such as conforming to SNOMED CT® terminology.

CONCLUSION

Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation. Although the subject matter has been described in language specific to structural features and/or methodological acts, the subject matter defined in the appended claims is not limited to the specific features or acts described above. Rather, the specific features and acts described above are disclosed as example forms of implementing the claims. This disclosure is intended to cover any and all adaptations or variations of the disclosed implementations, and the following claims should not be construed to be limited to the specific implementations disclosed in the specification. Instead, the scope of this document is to be determined entirely by the following claims, along with the full range of equivalents to which such claims are entitled.

The invention claimed is:

1. A system comprising:
one or more processors; and
one or more storage media storing processor-executable instructions that, when executed by the one or more processors, configure the system to perform operations comprising:
presenting a document in a documentation display area of a user interface;
presenting a list of external components in a macro display area of the user interface that is adjacent to the documentation display area, wherein an individual external component is configured to access a particular type of external medical data of a plurality of different types of external medical data accessible via the list of external components;
determining a patient identifier associated with the document;
receiving input, within the macro display area, that selects an external component from the list of external components, wherein selection of the external component initiates a macro that provides instructions to launch the selected external component;
launching, based at least in part on the macro, the selected external component in a launched external component display area of the user interface, the launched external component display area being presented contemporaneously with the documentation display area and the macro display area;
providing, to the launched external component, component-specific context data associated with the document thereby enabling the launched external component to access, via at least one remote storage location, external medical data of a particular type for a patient identified by the patient identifier;
displaying the accessed external medical data within the launched external component display area;
processing user interactions associated with the accessed external medical data displayed within the launched external component display area, the user interactions modifying the accessed external medical data to produce modified external medical data;
capturing a message sent from the launched external component to the at least one remote storage location, the message including at least a portion of the modified external medical data; and
automatically rendering a portion of the document presented in the documentation display area based at least in part on the portion of the modified external medical data included in the captured message.

2. The system according to claim 1, the operations further comprising monitoring inbound data and outbound data of the launched external component.

3. The system according to claim 2,
wherein the automatically rendering the portion of the document comprises updating information in the portion of the document.

4. The system according to claim 1, wherein the launched external component display area comprises a pop-up window within the user interface that enables the portion of the modified external medical data to be automatically rendered within the portion of the document.

5. The system according to claim 1, wherein the component-specific context data comprises a set of context parameters in a format specific to the launched external component.

6. A method comprising:
causing a document to be displayed in a documentation display area of a user interface; causing a plurality of macro options to be displayed in a macro display area of the user interface that is adjacent to the documentation display area, individual ones of the plurality of macro options being associated with different external components configured to access different types of external medical data;
determining an identifier associated with the document;
receiving, within the macro display area, a selection of a macro option from the plurality of macro options displayed, wherein selection of the macro option initiates a macro that provides instructions to launch an external component;
launching, based at least in part on the macro, the external component within a launched external component display area of the user interface, the launched external component display area being presented contemporaneously with the documentation display area and the macro display area;
providing, by at least one processor, component-specific context data of the document to the launched external component;
accessing, by the launched external component and via at least one remote storage location, external medical data of a particular type for a user identified by the identifier;
causing the accessed external medical data to be displayed within the launched external component display area, wherein the accessed external medical data corresponds to the component-specific context data of the document;
processing user interactions associated with the accessed external medical data displayed within the launched external component display area, the user interactions modifying the accessed external medical data to produce modified external medical data;
capturing a message sent from the launched external component to the at least one remote storage location, the message including at least a portion of the modified external medical data; and automatically rendering a portion of the document displayed in the documentation display area based at least in part on the portion of the modified external medical data included in the captured message.

7. The method according to claim 6, further comprising launching another external component in addition to the launching the external component, wherein the launched other external component accesses other external medical data of a type different than the particular type of the accessed external medical data.

8. The method according to claim 6, wherein the component-specific context data provided to the launched external component includes a set of context parameters that is configured to access the external medical data of the particular type and that is in a format specific to the launched external component.

9. The method according to claim 6, further comprising:
receiving a clipboard selection of a portion of the accessed external medical data;
adding the clipboard selection to a message queue for a rendering engine; and
rendering the clipboard selection into the document at a specified location.

10. The method according to claim 6, wherein
the automatically rendering the portion of the document comprises adding information from the message to the portion of the document.

11. The method according to claim 6, wherein the launched external component display area comprises a pop-up window within the user interface that enables the portion of the modified external medical data to be automatically rendered within the portion of the document.

12. The method according to claim 6, further comprising providing authorization information of a person preparing the document.

13. The method according to claim 6, further comprising rendering a layout of the portion of the document so that one or more first data fields are configured to receive structured data entry based on the automatic rendering and one or more second data fields are configured to receive unstructured data entry based on user input.

14. A computing device comprising:
at least one memory;
at least one processor in communication with the at least one memory; and
executable instructions stored on the at least one memory and executed on the at least one processor, to cause the computing device to:
cause a document to be displayed in a documentation display area of a user interface; cause a plurality of macros to be displayed in a macro display area of the user interface that is adjacent to the documentation display area, individual ones of the plurality of macros being configured to launch different external components within a launched external component display area of the user interface for accessing different types of external medical data;
determine an identifier associated with the document;
receive, within the macro display area, a selection that activates a macro of the plurality of macros;
launch, based at least in part on the selection, an external component within the launched external component display area of the user interface while the document is being displayed in the documentation display area of the user interface, the launched external component display area being presented contemporaneously with the documentation display area and the macro display area;
provide component-specific context data of the document to the launched external component;
access, by the launched external component and based at least in part on the component-specific context data, external medical data of a particular type from an external computing device, the external medical data being associated with a user identified by the identifier;
cause the accessed external medical data of the particular type to be displayed within the launched external component display area of the user interface;
process user interactions associated with the accessed external medical data displayed within the launched external component display area, the user interactions modifying the accessed external medical data to produce modified external medical data;
capture a message sent from the launched external component to the external computing device, the message including at least a portion of the modified external medical data; and
automatically render a portion of the document displayed in the documentation display area based at least in part on the portion of the modified external medical data included in the captured message.

15. The computing device according to claim 14, further comprising a monitoring agent, maintained on the at least one memory and executed on the at least one processor, to cause the computing device to:
monitor outbound messages sent by the launched external component to the external computing device; and
capture at least one outbound message sent from the launched external component to the external computing device for insertion into the document following triggering of the at least one outbound message by a user interacting with the launched external component.

16. The computing device according to claim 15, wherein:
the at least one outbound message is parsed for relevant information and a corresponding structured data message is placed into a message queue; and
the structured data message is rendered in the document by a rendering engine executed on the at least one processor.

17. The computing device according to claim 14, wherein the message is one of: a Health Level Seven (HL7) message; a Simple Object Access Protocol (SOAP) message; or a Hypertext Transfer Protocol (HTTP) message.

18. The computing device according to claim 14, wherein:
the macro is created by a user of the user interface; and
the user specifies, in the macro, data retrieval behavior of the launched external component.

19. The computing device according to claim 14, wherein:
the launched external component comprises a third party component; and
the launched external component display area comprises a pop-up window within the user interface that enables the portion of the modified external medical data to be automatically rendered within the portion of the document.

20. The computing device according to claim 14, wherein the accessed external data comprises one or more of:
patient radiology information;
patient electrocardiogram information;
patient allergy information;
patient lab information;
patient diagnosis information; or
patient pathology information.

* * * * *